(12) United States Patent
Gao et al.

(10) Patent No.: US 12,415,852 B2
(45) Date of Patent: Sep. 16, 2025

(54) MULTISPECIFIC ANTIBODY AND PREPARATION METHOD AND USE THEREOF

(71) Applicant: Mabnooah LLC., Sugar Land, TX (US)

(72) Inventors: Xin Gao, Beijing (CN); Niliang Qian, Beijing (CN); Hongjie Li, Beijing (CN); Cuima Yang, Beijing (CN); Fuyu Wang, Beijing (CN); Xiujie Pan, Beijing (CN); Yunhui Liu, Beijing (CN); Dongmei Hu, Beijing (CN)

(73) Assignee: Mabnooah LLC, Sugar Land, TX (US)

( * ) Notice: Subject to any disclaimer, the term of this patent is extended or adjusted under 35 U.S.C. 154(b) by 148 days.

(21) Appl. No.: 17/292,739

(22) PCT Filed: Jul. 8, 2020

(86) PCT No.: PCT/CN2020/100892
§ 371 (c)(1),
(2) Date: May 11, 2021

(87) PCT Pub. No.: WO2021/077806
PCT Pub. Date: Apr. 29, 2021

(65) Prior Publication Data
US 2021/0388077 A1 Dec. 16, 2021

(30) Foreign Application Priority Data
Oct. 24, 2019 (CN) .......................... 201911015236.1

(51) Int. Cl.
*C07K 16/24* (2006.01)
*C07K 16/28* (2006.01)

(52) U.S. Cl.
CPC .......... *C07K 16/241* (2013.01); *C07K 16/244* (2013.01); *C07K 16/2803* (2013.01); *C07K 16/2809* (2013.01); *C07K 16/2818* (2013.01); *C07K 16/2827* (2013.01); *C07K 16/2878* (2013.01); *C07K 2317/31* (2013.01); *C07K 2317/55* (2013.01); *C07K 2317/622* (2013.01); *C07K 2317/92* (2013.01)

(58) Field of Classification Search
CPC ................ C07K 16/241; C07K 16/244; C07K 16/2803; C07K 16/2809; C07K 16/2818; C07K 16/2827; C07K 16/2878; C07K 2317/31; C07K 2317/55; C07K 2317/622; C07K 2317/92
See application file for complete search history.

(56) References Cited

U.S. PATENT DOCUMENTS

| 5,677,425 A | 10/1997 | Bodmer et al. |
| 2011/0206660 A1 | 8/2011 | Blanchetot et al. |
| 2014/0194596 A1 | 7/2014 | Humphreys et al. |
| 2016/0176963 A1* | 6/2016 | Maurer .................. A61P 35/00 435/69.6 |
| 2017/0260271 A1* | 9/2017 | Igawa ..................... A61P 43/00 |

FOREIGN PATENT DOCUMENTS

| CN | 1842539 A | 10/2006 |
| CN | 101842387 A | 9/2010 |
| CN | 102099378 A | 6/2011 |
| CN | 103781801 A | 5/2014 |
| CN | 104321341 A | 1/2015 |
| CN | 104558191 A | 4/2015 |
| CN | 104592392 A | 5/2015 |
| CN | 106459220 A | 2/2017 |
| CN | 106661119 A | 5/2017 |
| CN | 107172880 A | 9/2017 |
| CN | 107266567 A | 10/2017 |
| CN | 107406497 A | 11/2017 |
| CN | 108473556 A | 8/2018 |
| CN | 108473568 A | 8/2018 |
| CN | 109563166 A | 4/2019 |

(Continued)

OTHER PUBLICATIONS

Gao et al. U.S. Appl. No. 18/036,144. (Unpublished) Fusion Protein Targeting Both CD3 and CD137, Preparation Method Therefor and Use Thereof. (Year: 2023).*
Liu et al. U.S. Appl. No. 18/838,155. (Unpublished) Fusion Protein of CD137 Antibody and CD40L and Use Thereof. (Year: 2024).*
Hussell (European Journal of Immunology (2001) 31: 2566-2573) (Year: 2001).*
Rayner (Journal of Biological Chemistry (2015) 290(13): 8420-8438) (Year: 2015).*
International Search Report issued in PCT/CN2020/100892, mailed Oct. 13, 2020.

(Continued)

*Primary Examiner* — Julie Wu
*Assistant Examiner* — Elizabeth A Shupe
(74) *Attorney, Agent, or Firm* — Leydig, Voit & Mayer, Ltd.

(57) ABSTRACT

The present application provides a multispecific antibody and preparation method and use thereof. The multispecific antibody comprises:
a) a Fab fragment specifically binding to a first antigen, wherein the Fab fragment consists of a light chain and CH1 and a variable region of a heavy chain;
b) a first peptide linker with the N-terminal end fused to the heavy chain;
c) a second peptide linker with the N-terminal end fused to the light chain,
wherein only one disulfide bond can be formed between the first and the second peptide linkers, and each of the first and the second peptide linkers is independently selected from the group consisting of a peptide linker comprising any of the sequences as set forth in SEQ ID NO.1-2, wherein x represents any amino acid other than Cys, or is absent.
The antibody can be readily produced by recombinant expression and can simultaneously target two different antigens or different epitopes of the same antigen, or multiple epitopes of more different antigens.

17 Claims, 6 Drawing Sheets

Specification includes a Sequence Listing.

(56) References Cited

FOREIGN PATENT DOCUMENTS

| | | | |
|---|---|---|---|
| CN | 110669137 A | 1/2020 | |
| EP | 2 281 845 A1 | 2/2011 | |
| JP | 2011-516084 A | 5/2011 | |
| JP | 2018-500315 A | 1/2018 | |
| WO | WO 92/22324 A1 | 12/1992 | |
| WO | WO 2005/000898 A2 | 1/2005 | |
| WO | WO 2009/040562 A1 | 4/2009 | |
| WO | 2009/131239 A1 | 10/2009 | |
| WO | WO 2009/126944 A1 | 10/2009 | |
| WO | WO 2011/117330 A1 | 9/2011 | |
| WO | WO 2013/026835 A1 | 2/2013 | |
| WO | WO 2013/124450 A1 | 8/2013 | |
| WO | WO-2015103549 A1 * | 7/2015 | ......... C07K 16/1063 |
| WO | WO 2015/145360 A1 | 10/2015 | |
| WO | WO 2015/181282 A1 | 12/2015 | |
| WO | WO 2015/197772 A1 | 12/2015 | |
| WO | WO 2016/001810 A1 | 1/2016 | |
| WO | 2016/100803 A2 | 6/2016 | |
| WO | WO 2016/097313 A1 | 6/2016 | |
| WO | WO 2017/093406 A1 | 6/2017 | |
| WO | WO 2017/102830 A1 | 6/2017 | |
| WO | WO 2017/186950 A1 | 11/2017 | |
| WO | WO-2018158727 A1 * | 9/2018 | ............... A61P 35/00 |
| WO | WO-2020243477 A2 * | 12/2020 | ....... A61K 39/39591 |

OTHER PUBLICATIONS

Johnson et al., Effector Cell Recruitment with Novel Fv-based Dual-affinity Re-targeting Protein Leads to Potent Tumor Cytolysis and in Vivo B-cell Depletion, Journal of Molecular Biology (2010) vol. 399(3), pp. 436-449.

Nolting, B., Linker Technologies for Antibody-Drug Conjugates, Methods in Molecular Biology (2013), vol. 1045, pp. 71-100.

Sasaki et al., IgG H chain [*Homo sapiens*], GenBank: BAN63150.1, GenBank, pp. 1-2, accessed Jul. 17, 2013.

Schoonjans et al., Fab Chains As an Efficient Heterodimerization Scaffold for the Production of Recombinant Bispecific and Trispecific Antibody Derivatives, Journal of Immunology (2000), vol. 165(12), pp. 7050-7057.

Ye Su et al., Construction and expression of disulphide stabilized anti-CD3/anti-Pgp diabody, Chinese Journal of Biotechnology (2009), vol. 25(7), pp. 1042-1048.

Wang et al., "Design and Production of Bispecific Antibodies", *Antibodies*, 8(3), 43, pp. 1-30 (2019).

European Patent Office, Office Action issued in counterpart European Patent Application No. 20 878 020.5, mailed on Aug. 7, 2023.

Davé et al., "Fab-dsFv: A bispecific antibody format with extended serum half-life through albumin binding", *mAbs*, 8(7): 1319-1335 (2016).

IMGT Scientific Chart, the International ImMunoGeneTics Information system, last updated: Jun. 8, 2016, accessed at web.archive.org/web/20191020131830/https:/www.imgt.org/IMGTScientificChart/Numbering/Hu_IGHGnber.html.

* cited by examiner

A

B

| antibody-antigen | affinity constant Kd(M) |
|---|---|
| E1/TNF-α Ag | 2.50E-08 |
| adalimumab/TNF-α Ag | 4.07E-08 |
| E1/IL-17A Ag | 5.31E-08 |
| secukinumab/IL-17A Ag | 2.18E-09 |
| E2/PD-L1 Ag | 2.96E-08 |
| E2/CD137 Ag | 1.46E-08 |
| E3/CD19 Ag | 1.56E-08 |
| E3/CD3ε Ag | 1.56E-07 |
| E4/ PD-L1 Ag | 3.10E-09 |
| E4/ CD137 Ag | 2.99E-07 |
| E5/ CD3ε Ag | 6.98E-10 |
| E5/ CD137 Ag | 4.91E-09 |
| E5/ PD-L1 Ag | 5.57E-10 |

Fig. 6

MULTISPECIFIC ANTIBODY AND PREPARATION METHOD AND USE THEREOF

CROSS REFERENCE TO RELATED APPLICATIONS

The application is the U.S. national phase of International Patent Application No. PCT/CN2020/100892, filed Jul. 8, 2020, which claims priority to Chinese Patent Application No. 201911015236.1, filed Oct. 24, 2019, each of which is hereby incorporated by reference in its entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 10,901 Byte ASCII (Text) file named "753931_3ST25.TXT," dated Jun. 13, 2024.

TECHNICAL FIELD

The present application relates generally to the field of antibodies. More specifically, the present application relates to a multispecific antibody and a preparation method and use thereof.

BACKGROUND OF THE INVENTION

It is well-known that natural antibody molecules are mostly divalent monospecific molecules. However, over the past half a century, many bispecific and multispecific antibody molecules have been artificially produced, thanks to advances in antibody engineering. Various forms thereof include, for example, a single chain Fv antibody (scFv, Huston et al., Proc. Natl. Acad. Sci. USA, 85:5879-5883 (1988)), a tetravalent IgG-scFv fusion (Coloma and Morrison, Nat. Biotechnol., 15:159-163(1997)), a diabody (Holliger et al., Proc. Natl. Acad. Sci. USA, 90:6444-6448 (1993)), a tandem scFv molecule (see, for example, Bargou et al., Science 321, 974-977(2008)), a tetravalent DVD-IG IgG-like double variable domain antibody (Wu et al., Nat. Biotechnol., 25:1290-1297(2007)), a tetravalent FIT-IG Fabs-In-Tandem immunoglobulin, (WO 2015/103072, Epimab Biotheraupeutics), a bivalent rat/mouse hybrid bispecific IgG (Lindhofer et al., J. Immunol., 155:219-225 (1995)), and a bispecific CROSSMAB binding protein (see, for example, WO 2013/026831 (Roche Glycart AG); WO 2014/167022 (Engmab AG)). Since bispecific or multispecific antibodies are capable of binding to two or more different epitopes or antigen targets, and possess new functions that are missing from certain linking molecules (see, e.g., Sergey et al., Drug Des Devel Ther. 12: 195-208 (2018)), thus bispecific or multispecific antibodies for the treatment of various tumors have received increasing attention, particularly the bispecific antibody for T cell redirection. Such a bispecific antibody can simultaneously target surface antigens on tumor cells and activating components of T-cell surface receptor (TCR) complexes, such as CD3, resulting in activation of cytotoxic T-lymphocytes (CTLs) that target tumors. A representative form of such a bispecific antibody is a "bi-specific T-cell engager" or "BITE antibody", for example, two scFv antibodies linked by a glycine-serine (G4S) linker, one of which provides a binding site for a tumor antigen (e.g., a 17-1A tumor antigen), while the other of which provides a binding site for a CD3 antigen on T cells (Mack et al., Proc. Natl. Acad. Sci. USA, 92: 7021-7025 (1995)). The anti-CD3×anti-CD19 BITE antibody—Blinatumomab has been approved by the U.S. Food and Drug Administration (FDA) for the treatment of unusual B-cell acute lymphoblastic leukemia (ALL). Other bispecific antibody forms for T cell redirection include, but are not limited to, a tetravalent tandem double chain antibody ("TandAb", Kipriyanov et al., J. Mol. Biol., 293:41-56 (1999); Arndt et al., Blood, 94:2562-2568 (1999)) and an amphiphilic DART dual-affinity re-targeting protein (Johnson et al., J. Mol. Biol., 399:436-449 (2010)).

It is well-known that the full-length bispecific antibody form containing Fc has a long half-life and has an Fc effector function. However, for the full-length bispecific antibody, knobs-into-holes ("KiH") technology (Ridgway et al., Protein Eng., 9: 617-621 (1996)) needs to be employed to improve heterodimerization assembly and stability of the Fc region, but poor heterodimer matching, light chain mismatching, etc., still result in poor stability of the target product and formation of a series of non-target products, thereby resulting in difficulties in molecular expression and purification. While Fc can confer a bispecific antibody a long half-life, it is also one of the reasons for interfering with heterodimer formation. Moreover, the Fc effector function is not necessary in certain drug designs, and also has an interfering effect on drug function. Thus, in order to avoid the effect of the Fc, some bispecific antibodies take advantage of single-chain forms, such as BITE antibodies, double-chain antibodies, DART proteins, and TandAb, to connect different variable domains through peptide linkers to achieve bispecificity. Compared to full-size monoclonal antibodies, these molecules have the advantages of being smaller and faster entry into tissues and tumors, along with the disadvantages that these forms do not contain the Fc region and generally have a molecular weight of less than 60 kDa, which leads to a very short in vivo half-life due to renal clearance, and are physically unstable (Spiess et al. (2015), supra). The Fc of a fill-length bispecific antibody results in the formation of inactive molecular by-products of unrelated heavy chain homodimer pairing, and a single-chain bispecific antibody has poor stability and a short half-life. Therefore, the double-chain Fab antibody form between these two forms is expected to overcome these problems at the same time. However, constructs obtained by directly fusing two or more Fab to each other via a common linker are not feasible because random association of two light chains still results in inactive, unwanted by-products.

A number of bispecific or multispecific antibody forms have been identified as possible forms for the development of new therapeutic antibodies. To date, however, no form has been able to provide a comprehensive set of properties that allow itself to be used to develop novel therapeutic antibodies for the treatment of most diseases. In view of the increasing potential applications of bispecific or multispecific antibodies and the variable results associated with currently available forms, there remains a need for improved forms that can be engineered to address specific challenges associated with developing antibodies for the treatment of specific diseases.

SUMMARY OF THE INVENTION

Provided herein are novel bispecific antibodies and methods of making them, which are readily produced due to reduced mismatching by-products and increased target products, and exhibit higher stability and less aggregation than the bispecific antibody fragments known in the art. Moreover, this method can be applied to existing antibodies without the need to screen for common light or heavy chains. In addition, this new bispecific antibody has a higher molecular weight than many single-chain bispecific antibody fragments, which can prevent excessive renal clearance, thereby increasing its in vivo half-life.

In a first aspect, the present application provides an antibody comprising:
- a) a Fab fragment specifically binding to a first antigen, wherein the Fab fragment consists of a light chain and CH1 and a variable region of a heavy chain;
- b) a first peptide linker with the N-terminal end fused to the heavy chain;
- c) a second peptide linker with the N-terminal end fused to the light chain, wherein only one disulfide bond can be formed between the first and the second peptide linkers, and each of the first and the second peptide linkers is independently selected from the group consisting of a peptide linker comprising any of the sequences as set forth in SEQ ID NO.1-2, wherein SEQ ID NO.1-2 are XPPCPAPE (SEQ ID NO: 1) and EPAPCPPX (SEQ ID NO: 2), respectively, and wherein X represents any amino acid other than Cys, or is absent.

In a second aspect, the application provides a nucleic acid encoding the antibody of the first aspect.

In a third aspect, the application provides an expression vector comprising the nucleic acid of the second aspect.

In a fourth aspect, the present application provides a host cell comprising the nucleic acid of the second aspect or the expression vector of the third aspect.

In some embodiments, the host cell is a mammal cell. Mammal cell includes, but is not limited to, a CHO cell, a NS0 cell, a SP2/0 cell, a HEK293 cell, a COS cell, and a PER.C6 cell.

In a fifth aspect, the present application provides a method of preparing the antibody of the first aspect, comprising:
- a) culturing the host cell of the fourth aspect; and
- b) recovering the antibody from the host cells or from the culture supernatant of the host cells.

In a sixth aspect, the application provides a pharmaceutical composition comprising the antibody of the first aspect, the nucleic acid of the second aspect, the expression vector of the third aspect, or the host cell of the fourth aspect, and a pharmaceutically acceptable carrier.

In a seventh aspect, the present application provides use of the antibody of the first aspect, the nucleic acid of the second aspect, the expression vector of the third aspect, or the host cell of the fourth aspect in the manufacture of a medicament for treating, ameliorating, or preventing a tumor, an autoimmune disease, or an infectious disease.

In an eighth aspect, the application provides a method for treating, ameliorating, or preventing a tumor, an autoimmune disease, or an infectious disease in a subject, comprising administering to the subject the antibody of the first aspect, the nucleic acid of the second aspect, the expression vector of the third aspect, or the host cell of the fourth aspect.

In a ninth aspect, the application provides the antibody of the first aspect, the nucleic acid of the second aspect, the expression vector of the third aspect, or the host cell of the fourth aspect for use in treating, ameliorating, or preventing a tumor, an autoimmune disease, or an infectious disease in a subject.

BRIEF DESCRIPTION OF THE DRAWINGS

FIG. 6 shows the measurements of affinity constants between each specific antibody constructed herein and their corresponding antigens.

DETAILED DESCRIPTION OF THE INVENTION

Figure 1:
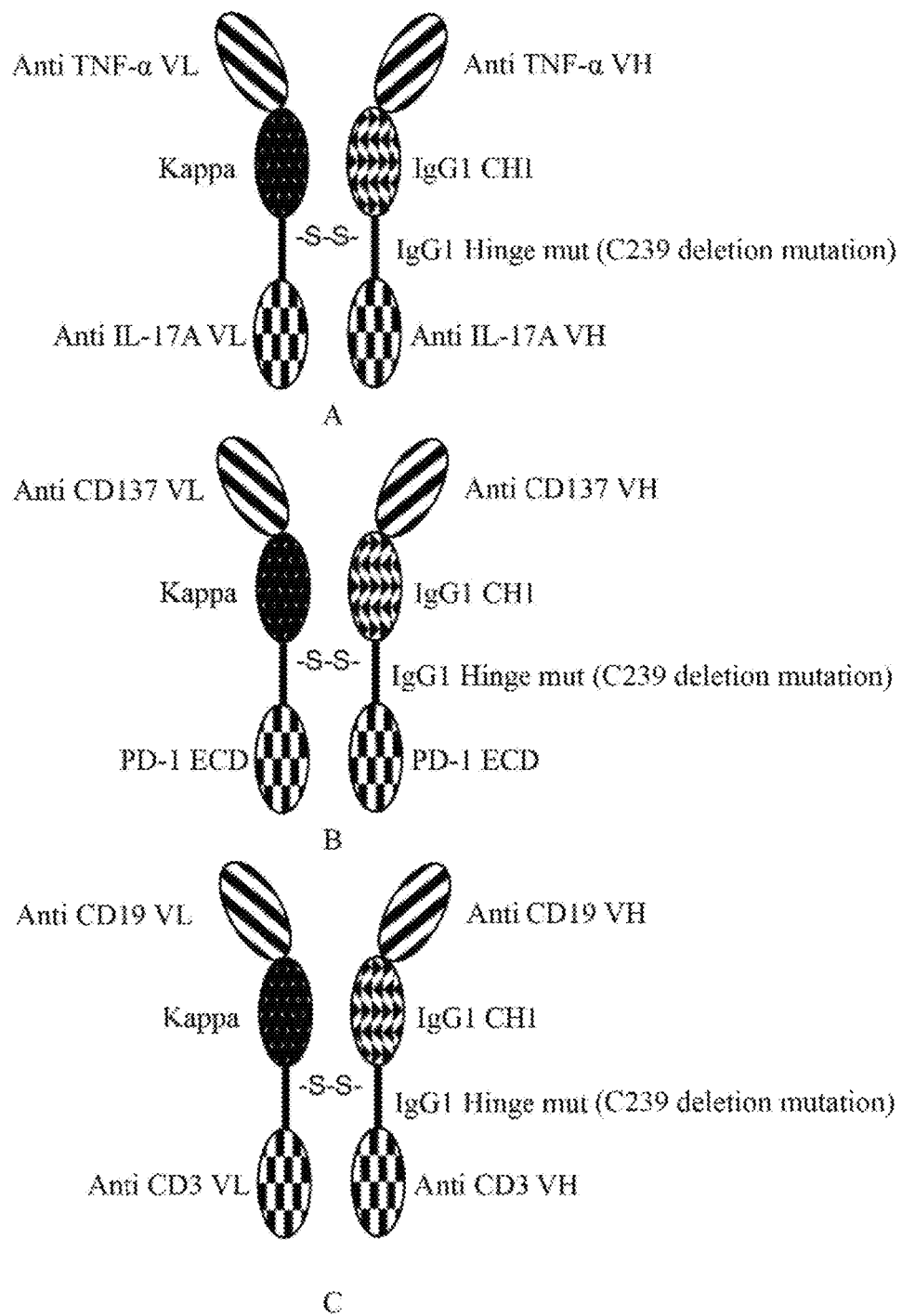
FIG. 1 shows a structural schematic of the bispecific or multispecific antibody constructed in the present application, in which A shows a structural schematic of an anti-TNFα×anti-IL-17A bispecific antibody (E1); B shows a structural schematic of anti-CD137×PD-1 ECD protein bispecific antibody (E2); C shows a structural schematic of anti-CD3×anti-CD19 bispecific antibody (E3); D shows a structural schematic of anti-PD-L1×anti-CD137 bispecific antibody (E4); E shows a structural schematic of anti-CD3× anti-CD137×PD-1 ECD protein trispecific antibody (E5).
Figure 1:
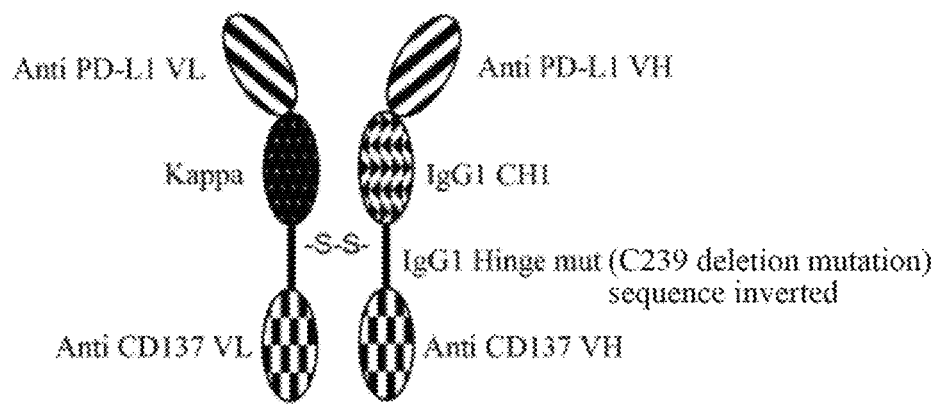
Figure 1:
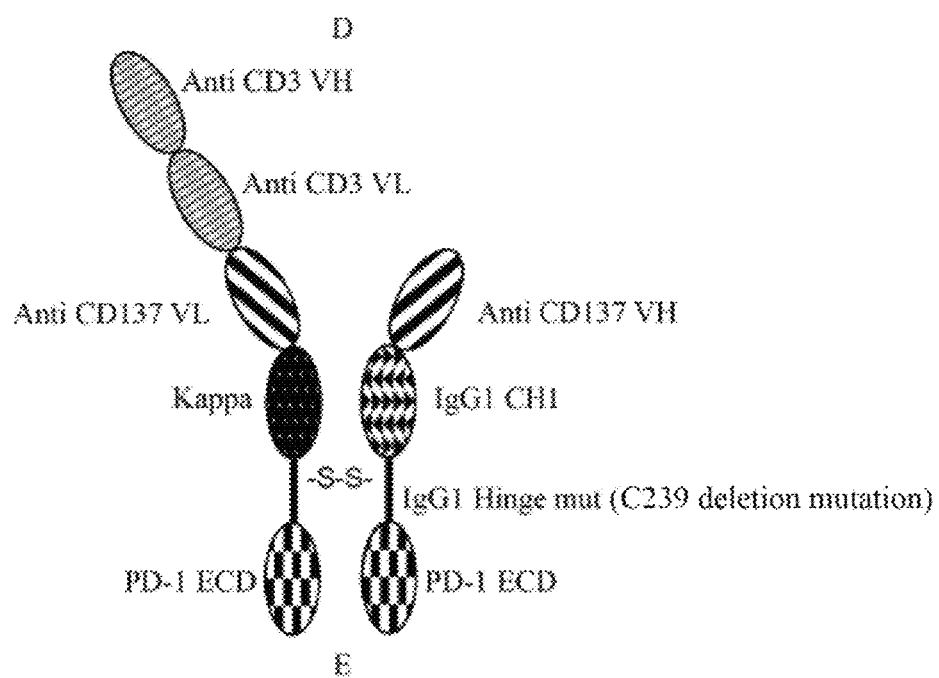

The following definitions and methods are provided to better define the application and to guide those of ordinary skill in the art in the practice of the application. Unless otherwise indicated, the terms of the application are to be understood in accordance with the usual usage of one of ordinary skill in the relevant art.

Definition

As used herein, the term "about" refers to ±10% of the recited number, e.g., about 1% refers to a range from 0.9% to 1.1%.

As used herein, the term "antibody" refers to any form of antibody or fragment thereof that exhibits the desired biological activity. Thus, it is used in its broadest sense and specifically covers monoclonal antibodies (including full-length monoclonal antibodies), polyclonal antibodies, multispecific antibodies (e.g., bispecific antibodies), and antibody fragments as long as they exhibit the desired biological activity. Thus, it will also be appreciated by those skilled in the art that the term "antibody" as used herein may also refer to a fusion protein of any form of the same or different antibodies or fragments thereof capable of exhibiting the desired biological activity, thereby achieving the function of multispecific antibodies.

As used herein, the term "antigen" refers to a molecule or portion thereof that is capable of being bound by a selective binding agent, such as an antibody, and can also be used in an animal to produce an antibody that is capable of binding to an epitope of the antigen. The antigen may have one or more binding epitopes. Antigens described herein may include, but are not limited to, most proteins, bacteria, viruses, bacterial exotoxins, polysaccharides (e.g., capsular polysaccharides of pneumonococcus), lipids, and the like.

As used herein, the term "specifically binding" is a term well-known in the art, and methods for determining such specifically binding of an antibody to an antigen are also well-known in the art. For example, in some embodiments, "specifically binding" refers to an antibody binding to the intended target, but not significantly binding to other targets. The antibody binds to the desired target epitope with significantly increased affinity and/or with a longer duration compared to binding to other epitopes.

As used herein, the term "antigen-binding fragment" includes a fragment or a derivative of an antibody that substantially retains its binding activity. Thus, the term "antigen-binding fragment" refers to a portion of a full-length antibody, typically an antigen-binding region or a variable region thereof. Examples of antigen-binding fragments include, but are not limited to, Fab fragments, Fab' fragments, F(ab')2 fragments, Fv fragments, diabodies, single chain antibody molecules such as scFv, and multi-specific antibodies formed from antibody fragments. It is also believed that antigen-binding fragments may include conservative amino acid substitutions that do not substantially alter their binding activity.

As used herein, the term "Fab fragment" encompasses a light chain and the CH1 and variable regions of a heavy chain. The heavy chain of the Fab molecule cannot form a disulfide bond with another heavy chain molecule.

As used herein, the term "Fab' fragment" contains a light chain and a portion or a fragment of a heavy chain that contains a VH domain and a CH1 domain and a region between the CH1 and CH2 domains such that an interchain disulfide bond can be formed between two heavy chains of two Fab' fragments to form an F(ab')2 molecule.

As used herein, the term "F(ab')2 fragment" contains two light chains and two heavy chains containing a portion of the constant region between the CH1 and CH2 domains such that an interchain disulfide bond is formed between the two heavy chains. The F(ab')2 fragment thus consists of two Fab' fragments which are linked together by a disulfide bond between the two heavy chains.

As used herein, the term "Fv fragment" encompasses variable regions from heavy and light chains, but lacks constant regions.

As used herein, the term "single chain Fv" or "scFv" refers to an antibody fragment comprising the VH and VL domains of an antibody, wherein these domains are present in a single polypeptide chain form. Typically, the Fv polypeptide further comprises a polypeptide linker between the VH and VL domains that enables the scFv to form the desired structure for antigen binding.

As used herein, the term "diabody" refers to a small antibody fragment having two antigen-binding sites, and the fragment comprising a heavy chain variable domain (VH) and a light chain variable domain (VL) (VH-VL or VL-VH) attached thereto in the same polypeptide chain. By using a linker that is too short to allow pairing between two domains on the same strand, each domain is forced to pair with the complementary domain of the other strand, thereby creating two antigen binding sites.

As used herein, the term "hypervariable region" refers to the amino acid residues of an antibody responsible for antigen binding. The hypervariable region comprises amino acid residues from "complementarity determining region" or "CDR" (e.g., residues 24-34 (LCDR-1), 50-56 (LCDR-2) and 89-97 (LCDR-3) in the light chain variable domain and residues 31-35(HCDR-1), 50-65(HCDR-2) and 95-102 (HCDR-3) in the heavy chain variable domain; Kabat et al., (1991) Sequences of Proteins of Immunological Interest, 5th edition, Public Health Service, National Institutes of Health, Bethesda, Md.), and/or amino acid residues from "hypervariable loop" (i.e., residues 26-32 (L1), 50-52 (L2), and 91-96 (L3) in the light chain variable domain and residues 26-32 (H1), 53-55 (H2), and 96-101 (H3) in the heavy chain variable domain; Chothia and Lesk, (1987) J. Mol. Biol. 196: 901-917. "framework region" or "FR" residues refer to those variable domain residues other than the hypervariable region residues defined herein as CDR residues.

As used herein, the term "peptide linker" refers to a relatively flexible peptide molecule used to link two polypeptides. The peptide linker used in the present application contains only one cysteine, so that a stable disulfide bond can be formed between the two peptide linkers.

As used herein, the term "binding moiety" refers to a moiety capable of specifically binding to other substances, which may include, but is not limited to, antibodies or antigen-binding fragments thereof, ligands and receptors, and the like. The antibody of the present application comprises a binding moiety that allows the antibody to target a target to which the binding moiety specifically binds.

As used herein, the term "tumor-associated antigen" refers to any molecule (e.g., a protein, a peptide, lipid, carbohydrate, etc.) that is expressed individually or predominantly or overexpressed by tumor cells to correlate the antigen with the tumor. A tumor-associated antigen may be an antigen which is only expressed by one type of tumors, such that the tumor antigen is only associated with or unique to one type of tumors. Alternatively, the tumor antigen may be associated with or unique to multiple types of tumors. For example, tumor-associated antigens can be expressed by both breast cancer cells and colon cancer cells, but not by normal, non-tumor or non-cancer cells. Exemplary tumor-associated antigens are tumor cell surface antigens, which are more advantageously recognized by therapeutic and diagnostic antibodies.

As used herein, the term "monoclonal antibody" refers to an antibody obtained from a population of substantially homogeneous antibodies, i.e., the antibodies constituting the population of antibodies are identical to each other, except that less variations that may occur naturally may be present. Monoclonal antibodies are highly specific for a single antigenic epitope. The monoclonal antibodies disclosed herein are not limited to antibody sources or methods of preparation thereof (e.g., by hybridomas, phage selection, recombinant expression, transgenic animals, etc.). The term includes intact immunoglobulins under the definition of "antibody" and fragments thereof, and the like.

An "expression vector" refers to a vector comprising a recombinant polynucleotide comprising an expression control sequence operably linked to a nucleotide sequence to be expressed. The expression vector comprises sufficient cis-acting elements for expression; Other elements for expression may be provided by a host cell or an in vitro expression system. Expression vectors include those known in the art, such as cosmids incorporating recombinant polynucleotides, plasmids (e.g., naked or contained in liposomes), and viruses (e.g., lentiviruses, retroviruses, adenoviruses, and adeno-associated viruses).

DETAILED DESCRIPTION

In general, a bispecific antibody fragment is constructed by linking the VL and VH of the antibody in series via the (G4S)n linker peptide, and it has poor stability, low gene expression level, aggregated expression products, and short in vivo half-life. It is well-known that the hinge region in the heavy chain of an antibody, on the one hand, is to provide a flexible structure to ensure that both arms of the antibody can sufficiently bind to the antigen, and, on the other hand, to provide two or more pairs of disulfide bonds to produce a stable homodimer structure. However, in the construction of the bispecific antibody, it is desirable to generate heterodimers as much as possible and reduce the homodimers. The conventional method is to introduce the knobs-into-holes structure through the amino acid mutation of CH3, or to introduce the amino acid with the opposite charges through the mutation to promote the formation of the heterodimer, but it is still not possible to solve the problem of the light chain mismatching. Furthermore, in some cases, no Fc effector function is required, and additional mutations are required to remove the effect of Fc, or the Fc is directly removed to obtain F (ab) 2 or Fab, which makes it difficult to introduce amino acid mutations that promote heterodimerization in the Fab segment. The present invention inventively makes use of the stabilizing effect of disulfide bonds in the antibody hinge region to fuse the mutated antibody hinge region to the C-terminal ends of the heavy and light chains of the Fab antibody, respectively, such that 1) only a pair of disulfide bonds is formed between the heavy and light chains at the mutated antibody hinge region, while a pair of disulfide bonds formed between the natural CH1 and CL is retained; 2) the non-covalent action of the heavy and light chain variable regions provides a superimposed stabilizing factor. Overall, the stability of homodimers between heavy chains is significantly reduced due to the absence of a second stabilizing factor (two pairs of disulfide bonds naturally occurring in the hinge region) and a third stabilizing factor (the Fc segment of the natural heavy chain, in particular the non-covalent dimerization of the CH3 moiety); However, the stability between the light and heavy chains is increased due to the addition of a pair of disulfide bonds, so that the stability of the light chain and the heavy chain heterodimer is much higher than that of the homodimer, and the heterodimer is extremely high in the expression product, and the homodimer is extremely low in the expression product, or even not stably generated. Trace amounts of heavy or light chain homodimers can be efficiently removed using affinity purification media for CH1 or CL. Therefore, by the present invention, stable high-purity target bispecific antibody can be easily obtained.

Thus, the present application provides improved bispecific or multispecific antibodies that can be readily produced by recombinant expression and that are capable of simultaneously targeting two different antigens or different epitopes of the same antigen, or multiple epitopes of more different antigens.

In a first aspect, the present application provides an antibody comprising:
a) a Fab fragment specifically binding to a first antigen, wherein the Fab fragment consists of a light chain and CH1 and a variable region of a heavy chain;
b) a first peptide linker with the N-terminal end fused to the heavy chain;
c) a second peptide linker with the N-terminal end fused to the light chain,
wherein only one disulfide bond can be formed between the first and the second peptide linkers, and each of the first and the second peptide linkers is independently selected from the group consisting of a peptide linker comprising any of the sequences as set forth in SEQ ID NO.1-2, wherein SEQ ID NO.1-2 are XPPCPAPE (SEQ ID NO: 1) and EPAPCPPX (SEQ ID NO: 2), respectively, and wherein X represents any amino acid other than Cys, or is absent.

In some embodiments, the first peptide linker and/or the second peptide linker may be the hinge region of a native antibody, wherein a deletion mutation may be made to the hinge region that retains only one cysteine.

In a preferred embodiment, the first peptide linker and/or the second peptide linker may be IgG1 hinge region with C239 deletion mutation.

In some embodiments, the first peptide linker and the second peptide linker are the same.

In some embodiments, the first peptide linker and the second peptide linker are different.

In some embodiments, each of the first and the second peptide linkers is independently selected from the group consisting of a peptide linker comprising Asp Lys Thr His Thr Pro Pro Cys Pro Ala Pro Glu Leu Leu Gly Gly Pro Ser (SEQ ID NO: 45) or Ser Pro Gly Gly Leu Leu Glu Pro Ala Pro Cys Pro Pro hr His Thr Lys Asp (SEQ ID NO: 46), and wherein the first and the second peptide linkers are the same.

The amino acid sequence of an antibody is numbered to identify equivalent positions, and there are currently a number of different numbering protocols for the antibody. The Kabat protocol (Kabat et al., 1991) was developed based on the positions of regions of high sequence variation between sequences of the same type of domains. Its numbers differ against the variable domains of the heavy (VH) and light (Vλ and Vκ) chains of an antibody. The Chothia protocol (Al-Lazikani, 1997) is identical to the Kabat protocol, but corrects the positions at which the annotation is inserted around the first VH complementarity determining region (CDR) so that they correspond to the structural ring. The antibodies in the present application are numbered according to the Kabat protocol.

In some embodiments, the antibody of the first aspect may be fused to another binding moiety through the C-terminal end of its first peptide linker and/or second peptide linker such that the binding valence of the antibody is bivalent or trivalent.

For example, the antibody of the first aspect may be fused to a first binding moiety through the C-terminal end of its first peptide linker or second peptide linker, thereby forming a bispecific antibody. The first binding moiety may be selected from an antibody or an antigen-binding fragment thereof, a ligand, and a receptor. In some embodiments, the antibody of the first aspect may be fused to a first binding moiety and a second binding moiety through the C-terminal ends of its first peptide linker and second peptide linker, respectively, to form a bispecific (in the case where the first binding moiety and the second binding moiety are the same) or trispecific antibody (in the case where the first binding moiety and the second binding moiety are different). The first binding moiety and the second binding moiety may each be independently selected from the group consisting of an antibody or an antigen-binding fragment thereof, a ligand, and a receptor.

In some embodiments, the antibody of the first aspect further comprises a third binding moiety that binds to the N-terminal end of the light or heavy chain of the Fab fragment. Preferably, the third binding moiety binds to the N-terminal end of the light chain of the Fab fragment.

In some embodiments, the first binding moiety is a heavy chain variable region (VH) of an antibody capable of specifically binding a second antigen, and the second binding moiety is a light chain variable region (VL) of an antibody capable of specifically binding a second antigen.

In some embodiments, the first binding moiety, the second binding moiety, and/or the third binding moiety may be independently selected from the group consisting of bivalent, trivalent, or more valent antibody fragments such that the final antibody is trivalent, tetravalent, or more valent. One skilled in the art may select a suitable antibody fragment to be fused to the first peptide linker and/or the second peptide linker as desired.

In some embodiments, the antigen binding fragment is selected from the group consisting of Fab fragments, Fab' fragments, F (ab')2 fragments, Fv fragments, diabodies, and single chain antibody molecules such as scFv.

The Fab fragment specifically binding to a first antigen, the first binding moiety, the second binding moiety, and the third binding moiety may each be independently derived from a monoclonal antibody.

In some embodiments, the monoclonal antibody used in the present application may be selected from one or more of the following: adalimumab, secukinumab, rituximab, trastuzumab, gemtuzumab ozogamicin, alemtuzumab, bevacizumab, cetuximab, panitumumab, ofatumumab, ipilimumab, brentuximab vedotin, denosumab, pertuzumab, obinutuzumab, ramucirumab, 3F8, abagovomab, adecatumumab, afutuzumab, alacizumab (pegol), amatuximab, apolizumab, bavituximab, bectumomab, belimumab, bivatuzumab, cantuzumab mertansine, cantuzumab (ravtansine), capromab (pendetide), catumaxomab, citatuzumab (bogatox), cixutumumab, clivatuzumab (tetraxetan), conatumumab, dacetuzumab, dalotuzumab, detumomab, drozitumab, ecromeximab, edrecolomab, elotuzumab, enavatuzumab, ensituximab, epratuzumab, ertumaxomab, etaracizumab, farletuzumab, FBTA05, flanvotumab, galiximab, gemtuzumab, ganitumab, girentuximab, glembatumumab (vedotin), ibritumomab tiuxetan, icrucumab, igovomab, indatuximab ravtansine, intetumumab, inotuzumab ozogamicin, ipilimumab (MDX-101), iratumumab, labetuzumab, lexatumumab, lintuzumab, lorvotuzumab (mertansine), lucatumumab, lumiliximab, mapatumumab, matuzumab, milatuzumab, mitumomab, mogamulizumab, moxetumomab (pasudotox), nacolomab (tafenatox), naptumomab (estafenatox), narnatumab, necitumumab, nimotuzumab, nivolumab, NR-LU-10, olaratumab, oportuzumab (monatox), oregovomab, panitumumab, pertuzumab, pritumumab, racotumomab, radretumab, robatumumab, omalizumab, sibrotuzumab, siltuximab, taplitumomab (paptox), tenatumomab, teprotumumab, ticilimumab, tremelimumab, tigatuzumab, tucotuzumab (celmoleukin), ublituximab, urelumab, veltuzumab, volociximab, votumumab and zalutumumab.

The antigens to which the antibodies of the present application bind may be a cell-associated protein, such as a cell surface protein on the membrane of a cell (T cell, endothelial cell, or tumor cell), or may be a soluble protein. The antigen may also be any of medically related proteins, such as those upregulated during disease or infection, such as receptors and/or their corresponding ligands. Specific examples of cell surface proteins include, but are not limited to, adhesion molecules such as integrins, E-selectin, P-selectin or L-selectin, CD2, CD3, CD4, CD5, CD7, CD8, CD11a, CD11b, CD18, CD19, CD20, CD23, CD25, CD33, CD38, CD40, CD45, CD69, CD134, ICOS, CD137, CD27, carcinoembryonic antigen (CEA), TCR, MHC-I-class and MHC-II-class antigens, VEGF, and receptors for these proteins. Soluble proteins include interleukins (e.g., IL-1, IL-2, IL-3, IL-4, IL-5, IL-6, IL-8, IL-12, IL-16, or IL-17), viral antigens (e.g., respiratory syncytial virus or cytomegalovirus antigens), immunoglobulins (e.g., IgE), interferons (e.g., interferon alpha, interferon beta, or interferon gamma), tumor necrosis factor alpha (TNFalpha), tumor necrosis factor beta, colony stimulating factors (e.g., G-CSF or GM-CSF), and platelet-derived growth factors (e.g., PDGF-alpha and PDGF-beta) and their receptors, as appropriate. Other antigens include bacterial cell surface antigens, bacterial toxins, viruses (e.g., influenza virus, EBV, HepA, B and C), bioterrorism reagents, radionuclides and heavy metals, and snake and spider toxins and toxins.

Other antigens to which the antibodies of the present application bind include serum carrier proteins, polypeptides that are recruited via cell-mediated effector functions, and nuclide chelating proteins.

In some embodiments, an antigen to which the antibody of the present application can bind is a tumor-associated antigen, including any one or more of CD20, HER2, EGFR, CD33, CD52, VEGF, CTLA-4, CD30, RANKL, HER2, VEGF-R2, Her3, A33 antigen, CD5, CD19, CD22, CD23 (IgE receptor), CA242 antigen, 5T4, VEGFR-1, CD33, CD37, CD40, CD44, CD51, CD52, CD56, CD74, CD80, CD152, CD200, CD221, CCR4, NPC-1C, vimentin, insulin-like growth factor-1 receptor (IGF-1R), alpha fetoprotein, carcinoembryonic antigen (CEA), integrin $\alpha_v\beta_3$, integrin $\alpha_5\beta_1$, fibroblast-activating protein, FAP-alpha, TAG-72, MUC1, MUC16, prostate-specific membrane antigen (PMSA), EGP40 pan-cancer antigen, glycoprotein EpCAM, programmed death-1, liver regenerating phosphatase 3 (PRL-3), Lewis-Y antigen, GD2, phosphatidylinositol glycan-3 (GPC3), and mesothelin.

The first binding moiety, the second binding moiety, and the third binding moiety each are independently selected from a ligand and a receptor. The ligand may be selected from the group consisting of PD-L1, EphrinA1, VEGF and EGF. The receptor may be correspondingly selected from the group consisting of PD-1, EphA2, VEGFR1 and EGFR.

"Receptor" refers to any biological macromolecule capable of binding to hormones, neurotransmitters, drugs, or intracellular signaling molecules and causing changes in cellular function. The receptor itself contains at least two activity sites: one recognizes and binds the ligand and the other is a functional activity site responsible for generating a response, which is generated only after binding to the ligand to form a binary complex and altering conformation, thereby initiating a series of biochemical reactions, ultimately leading to the biological effect of the target cell. The receptor specifically binds to its ligand. Generally, the extracellular region of a receptor serves as a binding moiety in the present application.

"Ligand" refers to any molecule capable of binding to its receptor. Most ligands are hydrophilic biomacromolecules, such as cytokines, protein polypeptide hormones, water-soluble hormones, prostaglandins, hydrophilic neurotransmitters, and the like. Since such ligand signaling molecules cannot penetrate into a cell through the target cell membrane, their receptors are located on the target cell membrane.

PD-1 (Programmed Death Receptor 1), an important immunosuppressive molecule, belongs to the immunoglobulin superfamily and is a membrane protein of 268 amino acid residues. Immunomodulation targeting PD-1 shows important significance against anti-tumors, anti-infection, anti-autoimmune diseases, and organ transplantation survival and the like. The ligand PD-L1 can also serve as a target, and the corresponding antibodies can also have the same function. PD-1 or PD-L1 serves as a binding moiety in the present application, such as a first binding moiety and/or a second binding moiety. Preferably, the extracellular region of PD-1, i.e., PD-1 ECD, acts as a binding moiety in the present application.

The CH2-CH3 domain can be introduced at the C-terminal end of the Fab of the antibody of the present application. The CH2-CH3 domain can be linked to a peptide linker or to the C-terminal end of the first binding moiety and/or the second binding moiety. The CH2-CH3 domain optionally promotes heterodimerization via KiH mutations, introduction of cysteine residues, introduction of one or more salt bridge mutations, and such addition results in increased stability of the heterodimer. Salt bridges herein include hydrogen bonds and electrostatic interactions, such as salt bridges that can occur between glutamic acid and lysine residues.

The heavy and light chains of a native antibody include a variable region (i.e., V region) and a constant region (i.e., C region), respectively. The constant region of the heavy chain and the constant region of the light chain are referred to as CH and CL, respectively. The CL lengths of different types (kappa or lamda) of Igs are substantially the same, but the CH lengths of different types of Igs are different, for example, IgG, IgA and IgD include CH1, CH2 and CH3, while IgM and IgE include CH1, CH2, CH3 and CH4.

In a second aspect, the present application provides a nucleic acid encoding the antibody of the first aspect.

In a preferred embodiment, the nucleic acid may be a codon optimized nucleic acid suitable for expression in host cells. For example, according to the degeneracy of the codon, it still encodes the same protein. Methods for codon optimization according to the host cells used are well-known to those skilled in the art.

In a third aspect, the present application provides an expression vector comprising the nucleic acid of the second aspect.

Any suitable expression vectors can be used. For example, prokaryotic cloning vectors include plasmids from E. coli, such as colEl, pCRl, pBR322, pMB9, pUC, pKSM, and RP4. Prokaryotic vectors also include phage DNA such as M13 and derivatives of other filamentous single-stranded DNA phages. An example of a vector useful for yeast is the 2µ plasmid. Suitable vectors for expression in mammal cells include the following well-known derivatives: SV-40, adenovirus, retrovirus-derived DNA sequences, and shuttle vectors derived from combinations of functional mammal vectors, such as those described above, and functional plasmid and phage DNA.

Additional eukaryotic expression vectors are known in the art (e.g., P J. Southern & P. Berg, J. Mol. Appl. Genet, 1:327-341 (1982); Subramani et al., Mol. Cell. Biol, 1: 854-864 (1981); Kaufmann & Sharp, "Amplification And Expression of Sequences Cotransfected with a Modular Dihydrofolate Reductase Complementary DNA Gene," J. Mol. Biol, 159:601-621 (1982); Kaufhiann & Sharp, Mol. Cell. Biol, 159:601-664 (1982); Scahill et al., "Expression And Characterization Of The Product Of A Human Immune Interferon DNA Gene In Chinese Hamster Ovary Cells," Proc. Nat'l Acad. Sci USA, 80:4654-4659 (1983); Urlaub & Chasin, Proc. Nat'l Acad. Sci USA, 77:4216-4220, (1980), which is incorporated herein by reference in its entirety).

Expression vectors useful in the invention comprise at least one expression control sequence operably linked to a DNA sequence or fragment to be expressed. The control sequence is inserted into a vector to control and regulate the expression of cloned DNA sequences. Examples of useful expression control sequences are the lac system, the trp system, the tac system, the trc system, the major operon and promoter region of the phage Lamda, the control region of the fd coat protein, the glycolytic promoter of the yeast, such as the promoter of 3-phosphoglycerate kinase, the promoter of the yeast acid phosphatase, such as Pho5, the promoter of the yeast alpha mating factor, and promoters derived from a polyomavirus, an adenovirus, a retrovirus, and a simian virus, such as the early and late promoters of SV40, and other sequences known to control gene expression of prokaryotic or eukaryotic cells and viruses or combinations thereof.

In a fourth aspect, the present application provides a host cell comprising the nucleic acid of the second aspect or the expression vector of the third aspect.

In some embodiments, the host cells are mammal cells. Mammal cells may include, but are not limited to, CHO cells, NS0 cells, SP2/0 cells, HEK293 cells, COS cells, and PER.C6 cells. One skilled in the art will be able to select suitable host cells as desired.

In a fifth aspect, the present application provides a method of preparing the antibody of the first aspect, comprising:
a) culturing the host cell of the fourth aspect; and
b) recovering the antibody from the host cells or from the culture supernatant of the host cells.

In a sixth aspect, the application provides a pharmaceutical composition comprising the antibody of the first aspect, the nucleic acid of the second aspect, the expression vector of the third aspect, or the host cell of the fourth aspect, and a pharmaceutically acceptable carrier.

The pharmaceutical composition of the sixth aspect may be prepared in a desired dosage form according to conventional methods in the pharmaceutical field. In some embodiments, the pharmaceutical composition is preferably a liquid or suspension dosage form.

In some embodiments, the pharmaceutically acceptable carrier is a carrier that does not impair the viability and function of an immune cell, and does not affect specific binding of an antibody or antigen-binding fragment thereof to an antigen, including, but not limited to, cell culture media, buffers, physiological saline, balanced salt solutions, and the like. Examples of buffers include isotonic phosphates, acetates, citrates, borates, carbonates, and the like. In particular embodiments, the pharmaceutically acceptable carrier is phosphate buffer containing 1% serum.

The antibodies and pharmaceutical compositions disclosed herein can be used to treat, ameliorate, or prevent a tumor, an autoimmune disease, or an infectious disease in a subject.

In a seventh aspect, the present application provides use of the antibody of the first aspect, the nucleic acid of the second aspect, the expression vector of the third aspect, or the host cell of the fourth aspect in the manufacture of a medicament for treating, ameliorating, or preventing a tumor, an autoimmune disease, or an infectious disease.

In an eighth aspect, the application provides a method for treating, ameliorating, or preventing a tumor, an autoimmune disease, or an infectious disease in a subject, comprising administering to the subject the antibody of the first aspect, the nucleic acid of the second aspect, the expression vector of the third aspect, or the host cell of the fourth aspect.

In a ninth aspect, the application provides the antibody of the first aspect, the nucleic acid of the second aspect, the expression vector of the third aspect, or the host cell of the fourth aspect for use in treating, ameliorating, or preventing a tumor, an autoimmune disease, or an infectious disease in a subject.

"Treatment" refers to both therapeutic treatment and prophylactic or preventive measures aimed at preventing or slowing (alleviating) the target pathology state or condition. Individuals in need of treatment include those in which the condition already exists, as well as those in which the condition will develop or is intended to be prevented. Thus, an individual to be treated herein has been diagnosed with or tend to have or predisposed to the condition.

As used herein, the term "individual" refers to mammal, including but not limited to primates, cattle, horse, pig, sheep, goat, dog, cat, and rodent such as rat and mouse. Preferably, mammal is a non-human primate or human. A particularly preferred mammal is human.

In certain embodiments, the tumor is primary cancer or metastatic cancer. In particular embodiments, the tumor is selected from the group consisting of lung cancer such as non-small cell lung cancer, colorectal cancer, bladder cancer, hematopoietic cancer such as leukemia, breast cancer, gastric cancer, adenocarcinoma of the gastro-oesophageal junction, B-lymphocyte type non-Hodgkin's lymphoma, Hodgkin's lymphoma, anaplastic large cell lymphoma, head and neck cancer such as head and neck squamous cell carcinoma, malignant glioma, renal cancer, melanoma, prostate cancer, bone cancer, bone giant cell tumor, pancreatic cancer, sarcoma, liver cancer, skin squamous cell carcinoma, thyroid cancer, cervical cancer, nasal pharynx cancer, endometrial cancer, or metastatic cancer of the above-mentioned tumor.

In certain embodiments, the autoimmune disease may include systemic lupus erythematosus, rheumatoid arthritis, scleroderma, systemic vasculitis, dermatomyositis, autoimmune hemolytic anemia, and the like.

In certain embodiments, the infectious disease includes respiratory tract contagion disease, gastrointestinal tract contagion disease, blood contagion disease, body surface contagion disease, sex contagion disease, and the like. In particular embodiments, the infectious disease may include, but is not limited to, influenza, tuberculosis, mumps, measles, pertussis, ascarid, bacterial dysentery, hepatitis A, hepatitis B, malaria, epidemic encephalitis B, filariasis, schistosomiasis, trachoma, rabies, tetanus, gonorrhea, syphilis, AIDS, and the like.

As used herein, a "therapeutically effective amount" can be determined as desired, and one of ordinary skill in the art can readily grasp the amount actually required, for example, depending on the weight, age, and condition of the patient.

In this specification and the claims, the terms "comprising," and "comprises" and "comprise" mean "including, but not limited to" and are not intended to exclude other parts, additions, components or steps.

It is to be understood that the features, characteristics, components, or steps described in a particular aspect, embodiment, or example of the invention are applicable to any other aspects, embodiments, or examples described herein, unless indicated otherwise.

The above disclosure generally describes the present application, which is further exemplified by the following examples. These examples are described for purposes of illustration only and are not intended to limit the scope of the application. Although specific terms and values are used herein, such terms and values are also to be understood as illustrative and do not limit the scope of the present application. Unless otherwise specified, experimental methods and techniques in this specification are those conventional in the art. For other materials and equipments, etc., not specifically noted by the manufacturer, they are generally routinely available commercially.

EXAMPLES

In the examples and comparative examples of the present application, the raw materials and the reagents as used are conventional and commercially available, unless otherwise specified.

The following vectors used in Examples 1 to 5 are recombinant vectors used as amplification templates in each Example: pQKD1101-TNFα, pQK1114-IL-17A, pUC57 IgG1 CH1-Hinge mut and pUC57 Kappa-Hinge mut, pUC57 human PD-L1 ECD, pQKZW106H IgG1 CH1-Hinge mut, pQKZW106L Kappa-Hinge mut, Triad5H, Triad5L, pUC57 PD-L1 VL-Kappa-Hinge mut, pUC57 PD-L1 VH-IgG1 CH1 Hinge mut, pUC57 PD-L1 VL-Kappa-Hinge mut, pUC57 anti CD3 scFv.

Example 1: Preparation, Expression and Identification of Anti-TNFα×Anti-IL-17A Bispecific Antibody Materials The VH and VL encoding nucleic acid sequences of the anti-TNFalpha monoclonal antibody adalimumab and the anti-IL-17A monoclonal antibody secukinumab were obtained by DNA synthesis (General Biosystem (Anhui) Co., Ltd.), and each encoding sequence was respectively inserted into expression vectors pQKD1101 (General Biosystem (Anhui) Co., Ltd.) and pQK1114 (General Biosystem (Anhui) Co., Ltd.) which were fully synthesized. The resulting products were referred to as pQKD1101-TNFalpha and pQK1114-IL-17A, respectively. The encoding nucleic acid sequences of IgG1 CH1-Hinge mut (i.e., the IgG1 hinge region with C239 deletion) and of Kappa-Hinge mut (i.e., the IgG1 hinge region with C239 deletion) were similarly obtained by DNA synthesis and cloned into the vector pUC57 (General Biosystem (Anhui) Co., Ltd.), respectively. The resulting products were referred to as pUC57 IgG1 CH1-Hinge mut (C239 deletion mutation) and pUC57 Kappa-Hinge mut (C239 deletion mutation), respectively.

The nucleotide sequences of IgG1 CH1-Hinge mut and Kappa-Hinge mut were as follows:

```
IgG1 CH1-Hinge mut nucleotide sequence
                              (SEQ ID NO: 3)
GCTAGCACCA AGGGCCCATC CGTCTTCCCC CTGGCACCCT

CCTCCAAGAG CACCTCTGGG GGCACAGCGG CCCTGGGCTG

CCTGGTCAAG GACTACTTCC CCGAACCGGT GACGGTGTCG

TGGAACTCAG GCGCCCTGAC CAGCGGCGTG CACACCTTCC

CGGCTGTCCT ACAGTCCTCA GGACTCTACT CCCTCAGCAG

CGTGGTGACC GTGCCCTCCA GCAGCTTGGG CACCCAGACC

TACATCTGCA ACGTGAATCA CAAGCCCAGC AACACCAAGG

TGGACAAGAA AGTTGAGCCC AAATCTTGTG ACAAAACTCA

CACACCACCG TGCCCAGCAC CTGAACTCCT GGGGGGACCG TCA

Kappa -Hinge mut nucleotide sequence
                              (SEQ ID NO: 4)
CGAACTGTGG CTGCACCATC TGTCTTCATC TTCCCGCCAT

CTGATGAGCA GTTGAAATCT GGAACTGCCT CTGTTGTGTG

CCTGCTGAAT AACTTCTATC CCAGAGAGGC CAAAGTACAG
```

```
TGGAAGGTGG ATAACGCCCT CCAATCGGGT AACTCCCAGG

AGAGTGTCAC AGAGCAGGAC AGCAAGGACA GCACCTACAG

CCTCAGCAGC ACCCTGACGC TGAGCAAAGC AGACTACGAG

AAACACAAAG TCTACGCCTG CGAAGTCACC CATCAGGGCC

TGAGCTCGCC CGTCACAAAG AGCTTCAACA GGGGAGAGTG

TGACAAAACT CACACACCAC CGTGCCCAGC ACCTGAACTC

CTGGGGGGAC CGTCA
```

1.1 Preparation of the Expression Vector for Anti-TNFα× Anti-IL-17A Bispecific Antibody 1.1.1 Construction of Heavy Chain Expression Vector pQKE1H of the Bispecific Antibody The anti-TNFalpha antibody VH, the anti-IL-17A antibody VH, and the IgG1 CH1-Hinge mut (C239 deletion mutation) were amplified by using pQKD1101-TNFalpha, pQK1114-IL-17A, and pUC57 IgG1 CH1-Hinge mut as templates, respectively, and using gold brand Mix PCR kit (TSINGKE Company) according to the instructions of manufacturer, the amplification products of which were about 0.4 kb, 0.42 kb, and 0.4 kb, respectively; The fully synthetic vector pQKX1 (General Biosystem (Anhui) Co., Ltd.) was digested with the restriction enzymes EcoRI (NEB, R3101S) and SapI (NEB, R0712S), and the resulting three PCR amplification products (ligation sequence from 5' to 3': anti-TNFalpha antibody VH-CH1-Hinge mut-anti-IL-17A antibody VH) and the digested vector were recombinantly ligated with BM seamless clone kit (Bormead) according to the instructions of manufacturer to obtain the heavy chain expression vector pQKE1H.

Primer airs for PCR amplification were as follows:

```
Amplification of anti-TNFalpha antibody VH fragment
TNFalpha-VH F
                                      (SEQ ID NO: 5)
5'- TGTGGCTGAGAGGTGCCAGATGTGAAGTGCAGCTGGTGGAGTC -
3'

TNFalpha-VH R
                                      (SEQ ID NO: 6)
5'- GACGGATGGGCCCTTGGTGCTAGCACTAGACACTGTGACCAGGGT
A -3'

Amplification of anti-IL-17A antibody VH fragment
IL-17A-VH F
                                      (SEQ ID NO: 7)
5'- CTGAACTCCTGGGGGGACCGTCATGTGAAGTGCAGCTGGTGGAA
T - 3'

1L-17A-VH R
                                      (SEQ ID NO: 8)
5'- TGATTATGATCAATGAATTCATCAGCTAGACACTGTCACCAGAGTG
C - 3'

Amplification of IgG1 CH1-Hinge mut (C239 deletion
mutation) fragment
Em1 CH1 hinge F
                                      (SEQ ID NO: 9)
5'- TACCCTGGTCACAGTGTCTAGTGCTAGCACCAAGGGCCCATCCG -
3'

Em1 CH1 hinge R
                                      (SEQ ID NO: 10)
5'- ATTCCACCAGCTGCACTTCACATGACGGTCCCCCCAGGAGTTCAG
G - 3'
```

1.1.2 Construction of Light Chain Expression Vector pQKE1L of the Bispecific Antibody The anti-TNFalpha antibody VL, the anti-IL-17A antibody VL, and the Kappa-Hinge mut (C239 deletion mutation) were amplified by using pQKD1101-TNFalpha, pQK1114-IL-17A, and pUC57 Kappa-Hinge mut as templates, respectively, and using gold brand Mix PCR kit (TSINGKE Company) according to the instructions of manufacturer, the amplification products of which were about 0.36 kb, 0.36 kb, and 0.42 kb, respectively; The fully synthetic vector pQKX2 (General Biosystem (Anhui) Co., Ltd.) was digested with the restriction enzymes EcoRI (NEB, R3101S) and SapI (NEB, R0712S), and the resulting three PCR amplification products (ligation sequence from 5' to 3': anti-TNFalpha antibody VL-Kappa-Hinge mut-anti-IL-17A antibody VL) and the digested vector were recombinantly ligated with BM seamless clone kit (Bormead) according to the instructions of manufacturer to obtain the light chain expression vector pQKE1L.

Primer pairs for PCR amplification were as follows:

```
Amplification of anti-TNF-alpha antibody VL
fragment
TNFalpha-VL F
                                      (SEQ ID NO: 11)
5'- TGTGGCTGAGAGGTGCCAGATGTGACATTCAGATGACTCAGA -
3'

TNFalpha-VL R
                                      (SEQ ID NO: 12)
5'- ACAGATGGTGCAGCCACAGTTCGCTTGATCTCGACTTTTGTGCCCT
G - 3'

Amplification of anti-IL-17A antibody VL fragment
IL-17A-VL F
                                      (SEQ ID NO: 13)
5'- CTGAACTCCTGGGGGGACCGTCAGAAATCGTCCTCACTCAGAGC -
3'

IL-17A-VL R
                                      (SEQ ID NO: 14)
5'- ATTATGATCAATGAATTCACTATTTGATCTCAAGCCGAGTGCCT -
3'

Amplification of Kappa-Hinge mut (C239 deletion
mutation) fragment
Em1 Cκ-hinge F
                                      (SEQ ID NO: 15)
5'- CAGGGCACAAAAGTCGAGATCAAGCGAACTGTGGCTGCACCATC -
3'

Em1 Cκ-hinge R
                                      (SEQ ID NO: 16)
5'-GGGCTCTGAGTGAGGACGATTTCTGACGGTCCCCCCAGGAGTTCAG
G - 3'
```

1.1.3 Amplification and Preparation of Recombinant Plasmid

The heavy chain expression vector pQKE1H and the light chain expression vector pQKE1L obtained as above were transformed into E. coli TOP10, respectively. After the clones were picked and identified, they were cultured in LB medium containing ampicillin (final concentration of 100 mg/L) for 16 hours at 37° C. with shaking under 200 rpm. Bacteria were collected by centrifugation at 8000×g for 20 minutes. The plasmid was isolated and extracted using NucleoBond Xtra Midi kit (Macherey-nagel) according to the instructions of manufacturer, and eluted with 1 mL of sterile ultrapure water. Finally, the plasmid concentration was determined using a Nanodrop microspectrophotometer.

1.2 Expression of Antibody

The heavy chain expression vector pQKE1H and the light chain expression vector pQKE1L were co-transfected into HEK293 cells for expression. Twenty-four hours prior to transfection, $1.5 \times 10^6$ of HEK293 (ATCC, No. CRL-1573) cells were seeded in a 500 mL flask containing 100 mL OPM-293 CD05 serum-free medium (Opmel, Cat: 81075-001) and cultured at 36.5° C., 7.5% $CO_2$, 120 rpm. At the time of transfection, the recombinant plasmids pQKE1H and pQKE1L were mixed in a 1:1 weight ratio (total DNA 100 µg) in 10 mL OPM-293 CD05 medium, followed by the addition of 100 µL PEI (concentration of 3 mg/mL), vortexed rapidly and incubated at the room temperature for 15 minutes. The mixture was then added to the above cell culture. Cells were further cultured for 7 days at 36.5° C., 7.5% $CO_2$, 120 rpm/min to obtain expressed antibodies. The antibody was the anti-TNFα×anti-IL-17A bispecific antibody expressed by the plasmids pQKE1H and pQKE1L. The antibody was designated as E1, and the structure was shown in FIG. 1A.

1.3 Purification of Antibody

Figure 2:
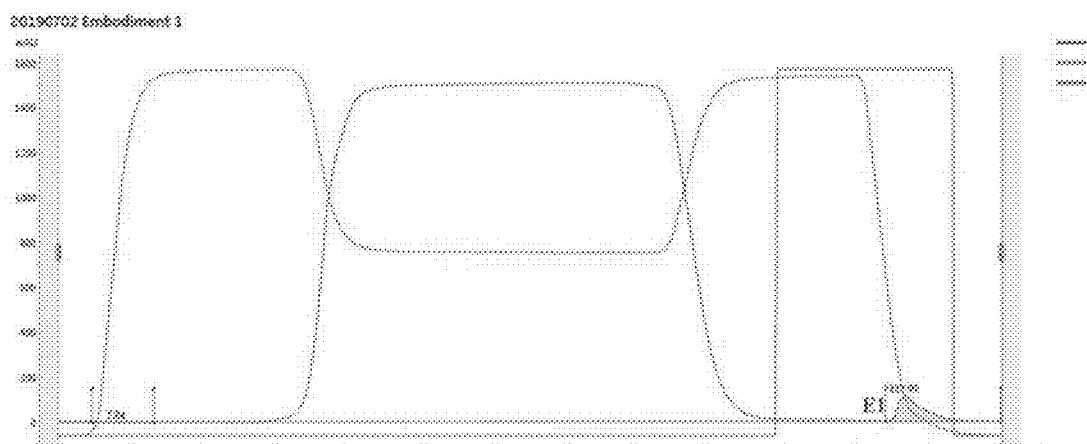
FIG. 2 shows the purification and SDS-PAGE electrophoresis results of the anti-TNFα×anti-IL-17A bispecific antibody (E1), in which A shows the Capto L affinity chromatogram of the antibody E1, B shows the SDS-PAGE electrophoresis results of the antibody E1: lane M is DNA Marker, lane 1 is the SDS-PAGE electrophoresis result under non-reducing condition, and lane 3 is the SDS-PAGE electrophoresis result under reducing condition.
Figure 2:
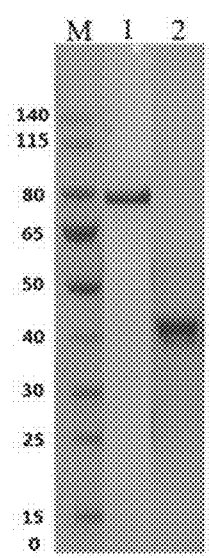

The harvested cell cultures were centrifuged at 3000×g for 20 min, and the supernatant was collected and filtered with a 0.45 µm filter. The 5 mL Capto L affinity column (GE) was equilibrated with the mixture buffer (pH 7.4) of 20 mM PB and 150 mM NaCl at a flow rate of 5 mL/min and a volume greater than 5CV. The filtered sample solution was loaded at a flow rate of 5 mL/min. After completion of the loading, the Capto L affinity column was washed with the mixture buffer (pH 7.4) of 20 mM PB and 150 mM NaCl at a flow rate of 5 mL/min. The elution was performed with 50 mM citric acid (pH 3.0) buffer at a flow rate of 5 mL/min and the complete elution peak was collected, while the pH of the collected eluate was adjusted to about 7.0 with 1M Tris HCl (pH 9.0) buffer (FIG. 2A). The purified product was ultra-filtered through an ultrafiltration tube and Tris-citric acid buffer was replaced with commercially available PBS buffer. The resulting protein was detected by SDS-PAGE and Coomassie Brilliant Blue staining (FIG. 2B), and the protein concentration was determined using a Nanodrop microspectrophotometer. The protein yield was calculated to be 55 mg/L.

1.4 Identification of Antibody 1.4.1 HPLC Determination of Antibody Purity

Figure 3:
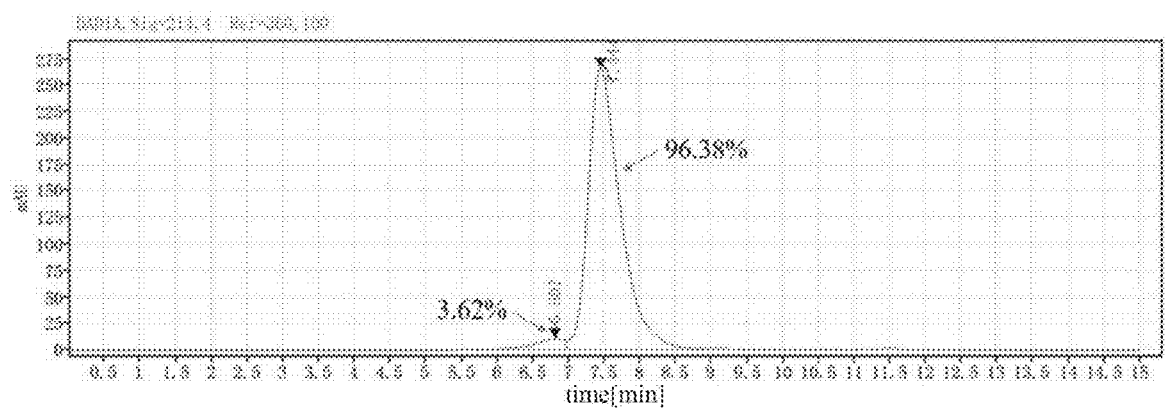
FIG. 3 shows the results of the purity detection of the antibody E1 by HPLC.

The purity of the antibody purified by Capto L was determined by HPLC (Agilent 1260 II) SEC. The chromatographic column was a Sepax water-soluble volume exclusion chromatographic column. The mobile phase was 50 mm PB+300 mm NaCl pH 7.0 with the loading amount of 10 g and the flow rate of 1 mL/min, and the isocratic elution was performed for 20 min. The results were shown in FIG. 3, and the monomer purity was ≥90%.

1.4.2 Fortebio Determination of Antibody Affinity

Figure 4:
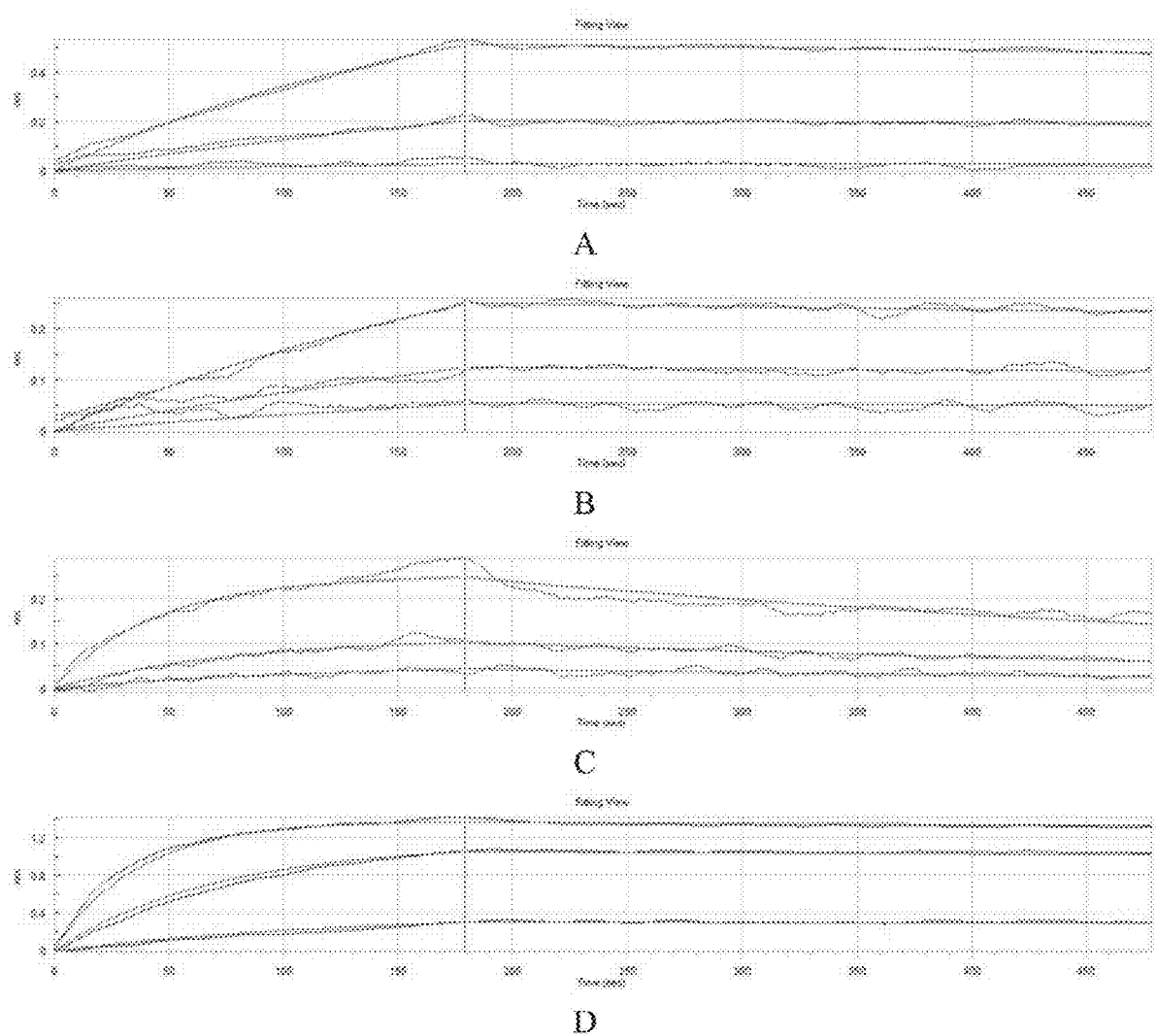
FIG. 4 shows the binding-dissociation curve for binding affinity as determined by Fortebio, in which A shows the binding-dissociation curve for the antibody E1 binding to the antigen TNF-alpha, B shows the binding-dissociation curve for adalimumab binding to the antigen TNF-alpha, C shows the binding-dissociation curve for the antibody E1 binding to the antigen IL-17A, and D shows the binding-dissociation curve for secukinumab binding to the antigen IL-17A.

The purified antibody was measured for its affinity constant $K_D$ using a molecular interactor Fortebio Octet QK (Molecular Devices). The E1 antibody and the control antibodies adalimumab (AbbVie) and secukinumab (Novartis) were immobilized by a sensor of Fab-Ch1 in a volume of 200 µL and at a concentration of 0.25 µM. The antigens human TNF-α (SinoBiological, Cat: 10602-H01H) and human IL-17A (SinoBiological, Cat: 12047-H07Y) were loaded at concentrations of 600 nM, 300 nM, 150 nM and 75 nM, respectively, in a total volume of 200 µL. The binding-dissociation curve was shown in FIG. 4 and the results for determination of affinity constant were shown in FIG. 6.

Example 2: Preparation, Expression and Identification of Anti-CD137×PD-1 ECD Protein Bispecific Antibody 2.1 Preparation of Expression Vector for Anti-CD137×PD-1 ECD Protein Bispecific Antibody The detailed procedures of expression vector construction and plasmid amplification were described in Example 1, in which the amplification template for the PD-1 ECD protein is pUC57 human PD-1 ECD containing the nucleic acid sequence of synthetic human PD-1 extracellular region inserted into the vector pUC57 (see NCBI database NP_005009.2 and reference Eszter Lázár-Molnár et al., "Structure-guided development of a high-affinity human Programmed Cell Death-1: Implications for tumor immunotherapy", EbioMedicine 17(2017) 30-44 for the nucleic acid sequence of human PD-1 extracellular region) (General Biosystem (Anhui) Co., Ltd.). A fully synthetic vector pQKZW106H IgG1 CH1-Hinge mut (General Biosystem (Anhui) Co., Ltd.) containing the VH portion of the heavy chain of the anti-CD137 antibody (see US-2019-0284292-A1 for the sequence) and the IgG1 CH1-Hinge mut (a hinge region having C239 deletion mutation) was digested with EcoRI and recombinantly ligated to the above-mentioned PCR product of pUC57 human PD-1 ECD after recovery (ligation sequence from 5' to 3': anti-CD137 antibody VH-CH1-Hinge mut-PD-1 ECD) to obtain a final heavy chain expression vector designated as pQKE2H; Similarly, the fully synthetic vector pQKZW106L Kappa-Hinge mut (General Biosystem (Anhui) Co., Ltd.) containing the VL portion of the light chain of the anti-CD137 antibody (see US-2019-0284292-A1 for the sequence) and Kappa-Hinge mut (a hinge region having C239 deletion mutation) was digested with EcoRI and recombinantly ligated to the above-mentioned PCR product of pUC57 human PD-1 ECD after recovery (ligation sequence from 5' to 3': anti-CD137 antibody VL-Kappa-Hinge mut-PD-1 ECD) to obtain a final light chain expression vector designated as pQKE2L.

The primer pairs used were as follows:

```
Amplification of PD-1 fragment linked to heavy and
light chains
Em2 PD-1 F
                                     (SEQ ID NO: 17)
5'- CTGAACTCCTGGGGGGACCGTCACCAGGATGGTTCTTAGACTC-
3'

Em2 PD-1 R
                                     (SEQ ID NO: 18)
5'-TGGCTGATTATGATCAATGAATTCTCACACCAGGGTTTGGAACTGGC
C-3'
```

2.2 Expression of Antibody

Transfection was performed according to the procedure described in Example 1. The cells to be transfected were HEK293 (ATCC No.: CRL-1573) and the transfection volume was 100 mL. The transfected cells were suspended in a 500 mL shake flask for 7 days under culture conditions of 36.5° C., 7.5% $CO_2$, 120 rpm/min and the antibody was harvested. The resulting antibody was the anti-CD137×PD-1 ECD protein bispecific antibody expressed by the plasmids pQKE2H and pQKE2L. The antibody was designated as E2, and the structure was shown in FIG. 1B.

2.3 Purification of Antibody

The purification was performed according to the procedure described in Example 1, and the protein concentration was determined by using a Nanodrop microspectrophotometer after buffer replacement. The protein yield was calculated to be 35 mg/L.

2.4 Identification of Antibody 2.4.1 HPLC Determination of Antibody Purity

Referring to Example 1, the purity of the antibody E2 was determined by HPLC, and the monomer purity was ≥90%.

2.4.2 Fortebio Determination of Antibody Affinity

The detailed procedure was described in Example 1. The E2 antibody was immobilized by a sensor of Fab-Ch1 at a concentration of 0.25 µM. The antigens human PD-L1 (SinoBiological, Cat: 10084-HNAH) and human CD137 (SinoBiological, Cat: 10041-H002H) were loaded at concentrations of 600 nM, 300 nM, 150 nM and 75 nM, respectively, in a total volume of 200 µL. The results for determination of affinity constant were shown in FIG. 6.

Figure 5:
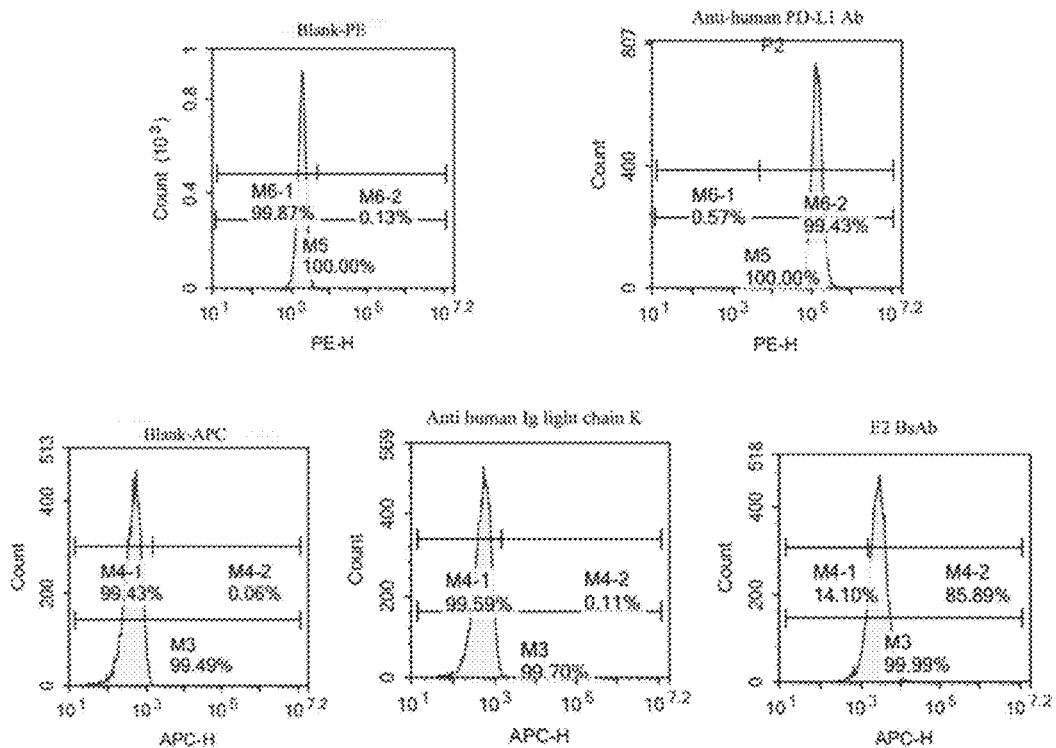
FIG. 5 shows flow cytometry results of the antibody E2 binding to the cell surface antigen, in which A shows flow cytometry results of the antibody E2 binding to MC38-PDL-1 cells and B shows flow cytometry results of the antibody E2 binding to B8-CD137 cells.
Figure 5:
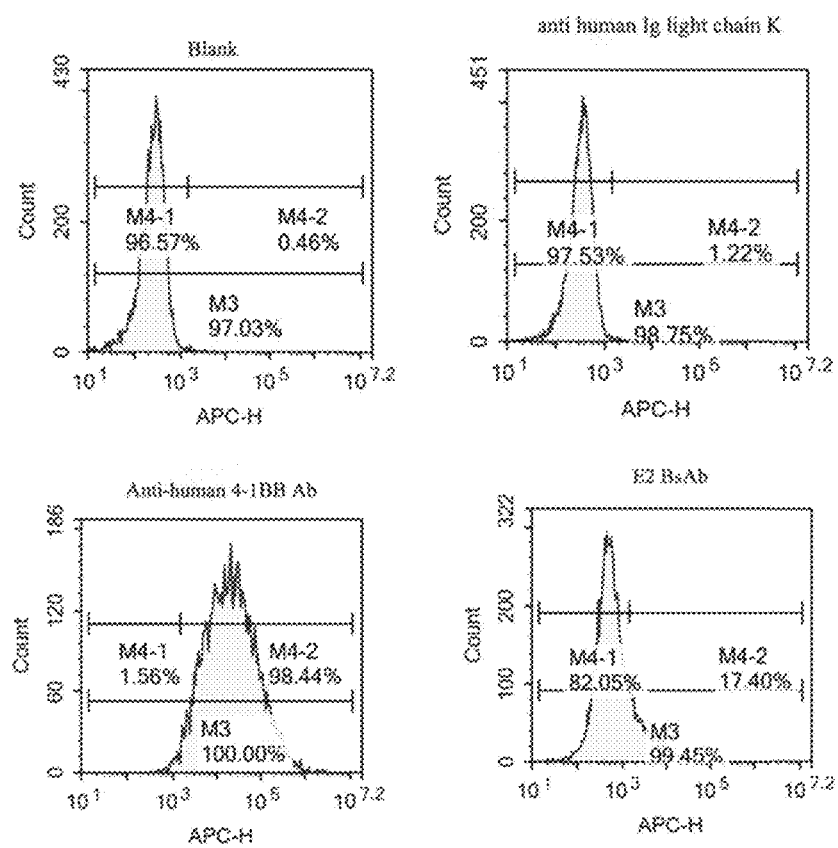

2.4.3 Detection of Antibody-Cell Binding Activity by Flow Cytometry 2.4.3.1 Binding Activity of Antibody to MC38-PD-L1 Cells Normally thawy MC38 cells (Xiehe Cell Resource Center, resource number: 3111C0001CCC000523) were passaged for at least 3, and the cells were passaged at 24 h before transfection and seeded in a 6-well plate. On the day of transfection, PEI (Sigma, Cat: 764647) and the synthetic plasmid pENTER PD-L1 (General Biosystem (Anhui) Co., Ltd.) were thawed to the room temperature. 5 µg of plasmid and 15 µg of PEI were added to 500 µl of DMEM medium (gibco, REF: 11965-092) and vortexed immediately for 15 min, and then the mixture was added dropwise to the cell culture medium and cultured in an incubator for further 24-48 h. DMEM medium containing 10% FBS and 2 µg/mL puromycin was exchanged after 48 h. Large-scale cell death occurred after 3 days, and the supernatant was discarded by gently flapping the walls of the plate. Well adherent cells were possibly stably transfected cells. After 8-10 days, the cells were digested and plated into 96-well plates depending on the growth state of the cells, and the monoclonal cell lines were screened. DMEM medium containing 2 µg/mL puromycin and 10% FBS was maintained under pressure. The resulting cell line was designated as MC38-PD-L1. The human PD-L1 extracellular domain gene was transformed into the genome of this cell line, which stably expressed the human PD-L1 extracellular domain protein and the protein was displayed on the cell membrane. MC-38-PD-L1 cells, which were thawed and cultured for more than 3 passages, were washed once with 10 mL PBS, trypsinized for 1 min at 1 mL 0.05%, and added to 4 mL 1640 medium containing 10% FBS. The cells were collected by centrifuging for 5 min at 1000 rpm/min, resuspended, and adjusted to a cell density of $1 \times 10^5$ cells/mL. The groups were set as a blank group, a positive control group, a secondary antibody group and an E2 group, and 10 µl of the above-mentioned cell suspension was added to the tubes of each group. 100 ng of E2 BsAb was added to the tube of the group E2, incubated at the room temperature for 30 min, washed with 3 mL of PBS buffer containing 4% FBS, centrifuged at 1000 rpm/min for 5 min, and resuspended in 50 µl of PBS buffer containing 4% FBS; 0.5 µl of water was added to the blank group; 0.5 µl of PE anti-human PD-L1 (BioLegend, clone number: 29E-2A3) was added to the positive control group; The groups E2 and secondary antibody were added with 0.5 µl of APC anti-human Ig light chain K (BioLegend, clone number: TB28-2). The mixture was incubated at the room temperature for 30 min in the dark. After completion of the incubation, the tubes of each group were washed with PBS buffer containing 4% FBS, centrifuged at 1000 rpm/min for 5 min, resuspended in 100 µl PBS buffer containing 4% FBS, and detected by flow cytometry (Ethan, instrument model: NovoCyte). The results were shown in FIG. 5A.

2.4.3.2 Binding Activity of Antibody to MC38-CD137 Cells

A MC38-CD137 cell is also an engineered cell line that is generated by integration of human CD137 into the genome of a MC38 cell (Xiehe Cell Resource Center, resource number: 3111C0001CCC000523) via steady-state transformation and is characterized by the ability to express human CD137 protein on cell membranes. The construction procedure of this cell line was described in 2.4.3.1 for MC38-PD-L1, except that the plasmid is pENTER CD137 (General Biosystem (Anhui) Co., Ltd.). The detailed procedure was described in 3.4.3.1, and the groups were set as a blank group, a positive control group, a secondary antibody group and an E2 group, respectively. The positive control group was added with 0.5 µl of APC anti-human 4-1BB, the secondary antibody group was added with 0.5 µl of APC anti-human Ig light chain K (BioLegend, clone number: TB28-2), and the E2 group was first added with 100 ng of E2 BsAb at room temperature for 30 minutes, washed and then added with 0.5 µl of APC anti-human Ig light chain K. All samples were incubated and re-washed and resuspended in 100 µl PBS buffer containing 4% FBS and detected by flow cytometry. The results were shown in FIG. 5B.

Example 3: Preparation, Expression and Identification of Anti-CD3×Anti-CD19 Bispecific Antibody 3.1 Preparation of Expression Vector for Anti-CD3×Anti-CD19 Bispecific Antibody The detailed procedures of expression vector construction and plasmid amplification were described in Example 1, in which Triad5H and pUC57 IgG1 CH1-Hinge mut were the templates for amplification of the heavy chain. Triad5H was a pre-synthesised plasmid (General Biosystem (Anhui) Co., Ltd.) containing the VH encoding nucleic acid sequences of the anti-CD19 monoclonal antibody of Blincyto (Amgen) and the anti-CD3 monoclonal antibody of Pasotuxizumab (Bayer) (General Biosystem (Anhui) Co., Ltd.). An anti-CD19 VH fragment and an anti-CD3 VH fragment were amplified by using Triad5H as a template, and an IgG1 CH1-Hinge mut (C239 deletion mutation) fragment was amplified by using pUC57 IgG1 CH1-Hinge mut as a template. The fully synthetic vector pQKX1 (General Biosystem (Anhui) Co., Ltd.) was digested with SapI and EcoRI, and the corresponding PCR products and digested products were recovered, and recombinantly ligated (ligation sequence from 5' to 3': anti-CD19 antibody VH-CH1-Hinge mut-anti-CD3 antibody VH) to obtain a final recombinant plasmid designated as pQKE3H. The Triad5L and pUC57 Kappa-Hinge mut were the templates for amplification of the light chain. Triad5L was a pre-synthesised plasmid (General Biosystem (Anhui) Co., Ltd.) containing the VL encoding nucleic acid sequences of the anti-CD19 monoclonal antibody of BITE diabody and the anti-CD3 monoclonal antibody of Pasotuxizumab (Bayer) (General Biosystem (Anhui) Co., Ltd.). An anti-CD19 VL fragment and an anti-CD3 VL fragment were amplified by using Triad5L as a template, and a Kappa-Hinge mut (C239 deletion mutation) fragment was amplified by using pUC57 Kappa-Hinge mut as a template. The fully synthetic vector pQKX2 was digested with SapI and EcoRI, and the corresponding PCR products and digested products were recovered, and recombinantly ligated (ligation sequence from 5' to 3': anti-CD19 antibody VL-Kappa-Hinge mut-anti-CD3 antibody VL) to obtain a final recombinant plasmid designated as pQKE3L.

The primer pairs used were as follows:

Amplification of anti-CD19 antibody VH fragment
Em3 CD19-VH F
(SEQ ID NO: 19)
5'- TGTGGCTGAGAGGTGCCAGATGTCAGGTTCAGTTGCAGCAGTCT -3'

Em3 CD19-VH R
(SEQ ID NO: 20)
5'- GACGGATGGGCCCTTGGTGCTAGCAGAAGAGACTGTCACTGTGGT - 3'

Amplification of anti-CD3 antibody VH fragment
Em3 CD3-VHF
(SEQ ID NO: 21)
5'- CCTGAACTCCTGGGGGGACCGTCAGAGGTGCAGCTGGTTGAATCT - 3'

Em3 CD3-VH R
(SEQ ID NO: 22)
5'- GATTATGATCAATGAATTCATCAGCTAGAAACTGTGACCAGTGT -3'

Amplification of IgG1 CH1-Hinge mut (C239 deletion mutation) fragment
Em3 CH1-hinge F
(SEQ ID NO: 23)
5'- GGCACCACAGTGACAGTCTCTTCTGCTAGCACCAAGGGCCCATCCG -3'

Em3 CH1-hinge R
(SEQ ID NO: 24)
5'- GCCAGATTCAACCAGCTGCACCTCTGACGGTCCCCCCAGGAGTTC - 3'

Amplification of anti-CD19 antibody VL fragment
Em3 CD19-VL F
(SEQ ID NO: 25)
5'- CTGTGGCTGAGAGGTGCCAGATGTGACATCCAGCTGACCCAGTC -3'

Em3 CD19-VL R
(SEQ ID NO: 26)
5'- GACAGATGGTGCAGCCACAGTTCGCTTGATTTCCAGCTTGGT -3'

Amplification of anti-CD3 antibody VL fragment
Em3 CD3-VL F
(SEQ ID NO: 27)
5'- CCTGAACTCCTGGGGGGACCGTCACAGACAGTGGTCACCCAAGAGC - 3'

Em3 CD3-VL R
(SEQ ID NO: 28)
5'- TGATTATGATCAATGAATTCACTACAAAACTGTCAGCTTGGTG -3'

Amplification of Kappa-Hinge mut (C239 deletion mutation) fragment
Em3 CK-hinge F
(SEQ ID NO: 29)
5'- GGAGGCACCAAGCTGGAAATCAAGCGAACTGTGGCTGCACCATC -3'

Em3 CK-hinge R
(SEQ ID NO: 30)
5'- AGGCTCTTGGGTGACCACTGTCTGTGACGGTCCCCCCAGGAGTTCAGG-3'

3.2 Expression of Antibody

Transfection was performed according to the procedure described in Example 1. The cells to be transfected were HEK293 (ATCC No.: CRL-1573) and the transfection volume was 100 mL. The transfected cells were suspended in a 500 mL shake flask for 7 days under culture conditions of 36.5° C., 7.5% $CO_2$, 120 rpm/min and the antibody was harvested. The resulting antibody was the anti-CD3×anti-CD19 bispecific antibody expressed by the plasmids pQKE3H and pQKE3L. The antibody was designated as E3, and the structure was shown in FIG. 1C.

3.3 Purification of Antibody

The purification was performed according to the procedure described in Example 1, and the protein concentration was determined by using a Nanodrop microspectrophotometer after buffer replacement. The protein yield was calculated to be 59 mg/L.

3.4 Identification of Antibody 3.4.1 HPLC Determination of Antibody Purity

Referring to Example 1, the purity of the antibody E3 was determined by HPLC, and the monomer purity was ≥90%.

3.4.2 Fortebio Determination of Antibody Affinity

The detailed procedure was described in Example 1. The E3 antibody was immobilized by a sensor of Fab-Ch1 at a concentration of 0.25 μM. The antigens human CD3 (Sino-Biological, Cat: 10977-H02H) and human CD19 (SinoBiological, Cat: 11880-H02H) were loaded at concentrations of 600 nM, 300 nM, 150 nM and 75 nM, respectively, in a total volume of 200 μL. The results for determination of affinity constant were shown in FIG. 6.

Example 4: Preparation, Expression and Identification of Anti-PD-L1×anti-CD137 Bispecific Antibody 4.1 Preparation of Expression Vector for the Anti-CD3× Anti-CD19 Bispecific Antibody The detailed procedures of expression vector construction and plasmid amplification were described in Example 1. The anti-PD-L1 VH-IgG1 CH1 Hinge mut and the anti-CD137 VH were amplified by respectively using the synthetic vector pUC57 PD-L1 VH-IgG1 CH1 Hinge mut (comprising the anti-PD-L1 VH encoding nucleic acid sequence and IgG1 CH1 Hinge mut (C239 deletion mutation and the hinge region D234-S252 inverted) encoding nucleic acid sequence of atezolizumab, Roche, produced by DNA synthesis (General Biosystem (Anhui) Co., Ltd.)) and the vector pQKZW106H IgG1 CH1-Hinge mut (General Biosystem (Anhui) Co., Ltd.). The vector pQKX1 (General Biosystem (Anhui) Co., Ltd.) was digested with SapI and EcoRI, and the corresponding PCR products and digested products were recovered, and recombinantly ligated (ligation sequence from 5' to 3': anti-PD-L1 antibody VH-CH1-Hinge mut-anti-CD137 antibody VH) to obtain a final recombinant plasmid designated as pQKE4H. The anti-PD-L1 VL-Kappa-Hinge mut and anti-CD137 VL fragment were amplified by respectively using the vector pUC57 PD-L1 VL-Kappa-Hinge mut (comprising the anti-PD-L1 VL encoding nucleic acid sequence and the Kappa-Hinge mut (C239 deletion mutation and the hinge region D234-S252 inverted) encoding nucleic acid sequence of atezolizumab produced by DNA synthesis (General Biosystem (Anhui) Co., Ltd.)) and the vector pQKZW106H IgG1 CH1-Hinge mut (General Biosystem (Anhui) Co., Ltd.). The vector pQKX2 (General Biosystem (Anhui) Co., Ltd.) was digested with SapI and EcoRI, and the corresponding PCR products and digested products were recovered, and recombinantly ligated (ligation sequence from 5' to 3': anti-PD-L1 antibody VL-Kappa-Hinge mut-anti-CD137 antibody VL) to obtain a final recombinant plasmid designated as pQKE4L.

IgG1 CH1-Hinge mut and Kappa-Hinge mut were as follows:

```
IgG1 CH1-Hinge mut D234-S252 inverted nucleotide
sequence
                                     (SEQ ID NO: 31)
GCTAGCACCA AGGGCCCATC CGTCTTCCCC CTGGCACCCT

CCTCCAAGAG CACCTCTGGG GGCACAGCGG CCCTGGGCTG

CCTGGTCAAG GACTACTTCC CCGAACCGGT GACGGTGTCG

TGGAACTCAG GCGCCCTGAC CAGCGGCGTG CACACCTTCC

CGGCTGTCCT ACAGTCCTCA GGACTCTACT CCCTCAGCAG

CGTGGTGACC GTGCCCTCCA GCAGCTTGGG CACCCAGACC

TACATCTGCA ACGTGAATCA CAAGCCCAGC AACACCAAGG

TGGACAAGAA AGTTGAGCCC AAATCTTGTT CACCGGGAGG

GCTGCTCGAA CCTGCACCAT GCCCGCCAAC ACACACTAAA GAC

Kappa -Hinge mut D234-S252 inverted nucleotide
sequence
                                     (SEQ ID NO: 32)
CGAACTGTGG CTGCACCATC TGTCTTCATC TTCCCGCCAT

CTGATGAGCA GTTGAAATCT GGAACTGCCT CTGTTGTGTG

CCTGCTGAAT AACTTCTATC CCAGAGAGGC CAAAGTACAG

TGGAAGGTGG ATAACGCCCT CCAATCGGGT AACTCCCAGG

AGAGTGTCAC AGAGCAGGAC AGCAAGGACA GCACCTACAG

CCTCAGCAGC ACCCTGACGC TGAGCAAAGC AGACTACGAG

AAACACAAAG TCTACGCCTG CGAAGTCACC CATCAGGGCC

TGAGCTCGCC CGTCACAAAG AGCTTCAACA GGGGAGAGTG

TTCACCGGGA GGGCTGCTCG AACCTGCACC ATGCCCGCCA

ACACACACTA AAGAC
```

The primer pairs used were as follows:

```
Amplification of anti-PD-L1 VH-IgG1 CH1 Hinge mut
fragment
PD-L1 VH-Hinge F
                                     (SEQ ID NO: 33)
5' - CTGTGGCTGAGAGGTGCCAGATGTGAGGTGCAGCTGGTTGAAT

C - 3'

PD-L1 VH-Hinge R
                                     (SEQ ID NO: 34)
5'-TGGCGGGCATGGTGCAGGTTCGAGCAGCCCTCCCGGTGAACAAGATT

TGGGCTCAACTTT - 3'

Amplification of anti-CD137 antibody VH fragment
Em4 CD137VH F
                                     (SEQ ID NO: 35)
5'-CTCGAACCTGCACCATGCCCGCCAACACACACTAAAGACGAAGTGCA

GCTGGTTCAGT-3'

Em4 CD137VH R
                                     (SEQ ID NO: 36)
5'- CTGATTATGATCAATGAATTCTCAAGAGGACACTGTGACCAGGGTG

C- 3'

Amplification of anti-PD-L1 VL-Kappa Hinge mut
fragment
PD-L1 VL-Hinge F
                                     (SEQ ID NO: 37)
5'- CTGTGGCTGAGAGGTGCCAGATGTGACATCCAGATGACCCAGT-3'

PD-L1
                                     (SEQ ID NO: 38)
5'-TGGCGGGCATGGTGCAGGTTCGAGCAGCCCTCCCGGTGAACACTCTC

CCCTGTTGAAGC- 3'

Amplification of anti-CD137 Antibody VL fragments
Em4 CD137VL F
                                     (SEQ ID NO: 39)
5'-CTCGAACCTGCACCATGCCCGCCAACACACACTAAAGACGACATCGT

GATGACCCAG-3'

Em4 CD137VL R
                                     (SEQ ID NO: 40)
5'-CTGATTATGATCAATGAATTCTCACTTGATTTCCACCTTGGTGCCTC

CG- 3'
```

4.2 Expression of Antibody

Transfection was performed according to the procedure described in Example 1. The cells to be transfected were HEK293 (ATCC No.: CRL-1573) and the transfection volume was 100 mL. The transfected cells were suspended in a 500 mL shake flask for 7 days under culture conditions of 36.5° C., 7.5% $CO_2$, 120 rpm/min and the antibody was harvested. The resulting antibody refers to the anti-PD-L1× anti-CD137 bispecific antibody expressed by the plasmids pQKE4H and pQKE4L. The antibody was designated as E4, and the structure was shown in FIG. 1D.

4.3 Purification of Antibody

The purification was performed according to the procedure described in Example 1, and the protein concentration was determined by using a Nanodrop microspectrophotometer after buffer replacement. The protein yield was calculated to be 38 mg/L.

4.4 Identification of Antibody 4.4.1 HPLC Determination of Antibody Purity

Referring to Example 1, the purity of the antibody E4 was determined by HPLC, and the monomer purity was ≥90%.

4.4.2 Fortebio Determination of Antibody Affinity

The detailed procedure was described in Example 1. The E4 antibody was immobilized by a sensor of Fab-Ch1 at a concentration of 0.25 μM. The antigens human PD-L1 (SinoBiological, Cat: 10084-HNAH) and human CD137 (SinoBiological, Cat: 10041-H002H) were loaded at concentrations of 600 nM, 300 nM, 150 nM and 75 nM, respectively, in a total volume of 200 μL. The results for determination of affinity constant were shown in FIG. 6.

Example 5: Preparation, Expression and Identification of Anti-CD3×Anti-CD137×PD-1 ECD Protein Trispecific Antibody 5.1 Preparation of Expression Vector for the Anti-CD3× Anti-CD137×PD-1 ECD Protein Trispecific Antibody The detailed procedures of expression vector construction and plasmid amplification were described in Example 1. The pQKE2H in Example 2 was used as the expression vector for the heavy chain; An anti-CD3 scFv fragment and an anti-CD137 VL-PD-1 ECD fragment were amplified by PCR using the pUC57 anti-CD3 scFv (which was obtained by inserting the VH-VL encoding nucleic acid sequence of an anti-CD3 monoclonal antibody (Pasotuxizumab, Bayer) produced by DNA synthesis (General Biosystem (Anhui) Co., Ltd.) into the expression vector pUC57) and the pQKE2L in Example 2 as templates, respectively. The pQKX2 vector (General Biosystem (Anhui) Co., Ltd.) was digested with SapI and EcoRI, and the two recovered PCR products and digested products were recombinantly ligated (ligation sequence from 5' to 3': anti-CD3 scFv-anti-CD137VL-Kappa-Hinge mut-PD-1 ECD) to obtain a final recombinant plasmid designated as pQKE5L.

The primer pairs used were as follows:

```
Amplification of anti-CD3 scFv fragment
CD3 scFv F
                                     (SEQ ID NO: 41)
5'- CTGTGGCTGAGAGGTGCCAGATGTGAGGTGCAGCTGGTTGAATCTG
GC- 3'

CD3 scFv R
                                     (SEQ ID NO: 42)
5'- GGAGACTGGGTCATCACGATGTCCAAAACTGTCAGCTTGGTGCCTC
C - 3'

Amplification of anti-CD137 VL-PD-1 ECD fragment
E2 LF
                                     (SEQ ID NO: 43)
5' - AGGCACCAAGCTGACAGTTTTGGACATCGTGATGACCCAGTCTCC
AG -3'

E2 LR
                                     (SEQ ID NO: 44)
5'- CTGATTATGATCAATGAATTCTCACACCAGGGTTTGGAACTGGCCG
GCT- 3'
```

5.2 Expression of Antibody

Transfection was performed according to the procedure described in Example 1. The cells to be transfected were HEK293 (ATCC No.: CRL-1573) and the transfection volume was 100 mL. The transfected cells were suspended in a 500 mL shake flask for 7 days under culture conditions of 36.5° C., 7.5% $CO_2$, 120 rpm/min and the antibody was harvested. The resulting antibody refers to the anti-CD3× anti-CD137×PD-1 ECD protein trispecific antibody expressed by the plasmids pQKE5H and pQKE5L. The antibody was designated as E5, and the structure was shown in FIG. 1E.

5.3 Purification of Antibody

The purification was performed according to the procedure described in Example 1, and the protein concentration was determined by using a Nanodrop microspectrophotometer after buffer replacement. The protein yield was calculated to be 11 mg/L.

5.4 Identification of Antibody 5.4.1 HPLC Determination of Antibody Purity

Referring to Example 1, the purity of the antibody E5 was determined by HPLC, and the monomer purity was ≥90%.

5.4.2 Fortebio Determination of Antibody Affinity

The detailed procedure was described in Example 1. The E5 antibody was immobilized by a sensor of Fab-Ch1 at a concentration of 0.25 μM. The antigens human CD3 (SinoBiological, Cat: 10977-H02H), human CD137 (SinoBiological, Cat: 10041-H002H) and human PD-L1 (SinoBiological, Cat: 10084-HNAH) were loaded at concentrations of 600 nM, 300 nM, 150 nM and 75 nM, respectively, in a total volume of 200 μL. The results for determination of affinity constant were shown in FIG. 6.

While the technical solutions of the present application have been described in detail with reference to the general description and specific embodiments, it will be apparent to those skilled in the art that modifications and alterations may be made thereto. Accordingly, such modifications and alterations which do not depart from the spirit of the invention are intended to be within the scope of the invention as claimed herein.

---

What is claimed is:

1. An antibody comprising:

a) a Fab fragment specifically binding to a first antigen, wherein the Fab fragment consists of a light chain, and CH1 and a variable region of a heavy chain;

b) a first peptide linker with the N-terminal end fused to the heavy chain;

c) a second peptide linker with the N-terminal end fused to the light chain, wherein only one disulfide bond can be formed between the first and the second peptide linkers, and each of the first and the second peptide linkers is independently selected from the group consisting of a peptide linker comprising Asp Lys Thr His Thr Pro Pro Cys Pro Ala Pro Glu Leu Leu Gly Gly Pro Ser (SEQ ID NO: 45) or Ser Pro Gly Gly Leu Leu Glu Pro Ala Pro Cys Pro Pro Thr His Thr Lys Asp (SEQ ID NO: 46), and wherein the first and the second peptide linkers are the same, wherein the antibody further comprises a first binding moiety fused to the C-terminal end of the first peptide linker, and a second binding moiety fused to the C-terminal end of the second peptide linker, wherein the first binding moiety is a heavy chain variable region (VH) of an antibody specifically binding to a second antigen, and the second binding moiety is a light chain variable region (VL) of the antibody specifically binding to the second antigen, or the first binding moiety is a light chain variable region (VL) of the antibody specifically binding to the second antigen; and the second binding moiety is a heavy chain variable region (VH) of the antibody specifically binding to the second antigen.

2. The antibody of claim 1, wherein the antibody further comprises a third binding moiety that binds to the N-terminal end of the light or heavy chain of the Fab fragment, and wherein the third binding moiety is selected from the group consisting of an antigen-binding fragment of an antibody specifically binding to a third antigen, a ligand and a receptor.

3. The antibody of claim 2, wherein the antigen-binding fragment is selected from the group consisting of a Fab fragment, a Fab' fragment, a F(ab')2 fragment, a Fv fragment, a diabody and sc-Fv.

4. The antibody of claim 3, wherein the third binding moiety is a sc-Fv.

5. The antibody of claim 2, wherein the first, the second, and the third antigens are independently selected from the group consisting of TNF alpha, IL17, CD137, CD3, CD19 and PD-L1.

6. A nucleic acid encoding an antibody, wherein the antibody comprises:
   a) a Fab fragment specifically binding to a first antigen, wherein the Fab fragment consists of a light chain, and CH1 and a variable region of a heavy chain;
   b) a first peptide linker with the N-terminal end fused to the heavy chain;
   c) a second peptide linker with the N-terminal end fused to the light chain,
   wherein only one disulfide bond can be formed between the first and the second peptide linkers, and each of the first and the second peptide linkers is independently selected from the group consisting of a peptide linker comprising Asp Lys Thr His Thr Pro Pro Cys Pro Ala Pro Glu Leu Leu Gly Gly Pro Ser (SEQ ID NO: 45) or Ser Pro Gly Gly Leu Leu Glu Pro Ala Pro Cys Pro Pro Thr His Thr Lys Asp (SEQ ID NO: 46), and wherein the first and the second peptide linkers are the same,
   wherein the antibody further comprises a first binding moiety fused to the C-terminal end of the first peptide linker and a second binding moiety fused to the C-terminal end of the second peptide linker, wherein the first binding moiety is a heavy chain variable region (VH) of an antibody specifically binding to a second antigen, and the second binding moiety is a light chain variable region (VL) of the antibody specifically binding to the second antigen, or the first binding moiety is a light chain variable region (VL) of the antibody specifically binding to the second antigen; and the second binding moiety is a heavy chain variable region (VH) of the antibody specifically binding to the second antigen.

7. An expression vector comprising the nucleic acid of claim 6.

8. A host cell comprising the nucleic acid of claim 6.

9. A pharmaceutical composition comprising the antibody of claim 1, and a pharmaceutically acceptable vector.

10. A method for treating or, ameliorating a tumor, an autoimmune disease or an infectious disease in a subject, comprising administering to the subject an antibody, wherein the antibody comprises:
   a) a Fab fragment specifically binding to a first antigen, wherein the Fab fragment consists of a light chain, and CH1 and a variable region of a heavy chain;
   b) a first peptide linker with the N-terminal end fused to the heavy chain;
   c) a second peptide linker with the N-terminal end fused to the light chain,
   wherein only one disulfide bond can be formed between the first and the second peptide linkers, and each of the first and the second peptide linkers is independently selected from the group consisting of a peptide linker comprising Asp Lys Thr His Thr Pro Pro Cys Pro Ala Pro Glu Leu Leu Gly Gly Pro Ser (SEQ ID NO: 45) or Ser Pro Gly Gly Leu Leu Glu Pro Ala Pro Cys Pro Pro Thr His Thr Lys Asp (SEQ ID NO: 46), and wherein the first and the second peptide linkers are the same,
   wherein the antibody further comprises a first binding moiety fused to the C-terminal end of the first peptide linker, and a second binding moiety fused to the C-terminal end of the second peptide linker, wherein the first binding moiety is a heavy chain variable region (VH) of an antibody specifically binding to a second antigen, and the second binding moiety is a light chain variable region (VL) of the antibody specifically binding to the second antigen, or the first binding moiety is a light chain variable region (VL) of the antibody specifically binding to the second antigen; and the second binding moiety is a heavy chain variable region (VH) of the antibody specifically binding to the second antigen.

11. The method of claim 10, wherein the tumor is selected from the group consisting of lung cancer, colorectal cancer, bladder cancer, leukemia, breast cancer, gastric cancer, adenocarcinoma of the gastro-oesophageal junction, B lymphocyte type non-Hodgkin's lymphoma, Hodgkin's lymphoma, anaplastic large cell lymphoma, head and neck cancer, malignant glioma, renal cancer, melanoma, prostate cancer, bone cancer, pancreatic cancer, sarcoma, liver cancer, skin squamous cell carcinoma, cervical cancer, nasal pharynx cancer, endometrial cancer, or metastatic cancer of the above tumors.

12. A host cell comprising the expression vector of claim 7.

13. A method for treating or ameliorating a tumor, an autoimmune disease or an infectious disease in a subject, comprising administering to the subject the expression vector of claim 7.

14. The method of claim 10, wherein the subject is human.

15. The antibody of claim 2, wherein the ligand is selected from the group consisting of PD-L1, EphrinA1, VEGF and EGF, and the receptor is correspondingly selected from the group consisting of PD-1, EphA2, VEGFR1 and EGFR.

16. The method of claim 10, wherein the autoimmune disease is selected from the group consisting of systemic lupus erythematosus, rheumatoid arthritis, systemic vasculitis and autoimmune hemolytic anemia.

17. The method of claim 10, wherein the infectious disease is selected from the group consisting of influenza, hepatitis B, rabies, syphilis, and AIDS.

* * * * *

SEQUENCE LISTING

```
<160> NUMBER OF SEQ ID NOS: 46

<210> SEQ ID NO 1
<211> LENGTH: 8
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is any amino acid other than Cys, or is
      absent

<400> SEQUENCE: 1

Xaa Pro Pro Cys Pro Ala Pro Glu
1               5

<210> SEQ ID NO 2
<211> LENGTH: 8
<212> TYPE: PRT
<213> ORGANISM: Artificial Sequence
<220> FEATURE:
<223> OTHER INFORMATION: synthetic
```

```
<220> FEATURE:
<221> NAME/KEY: MISC_FEATURE
<222> LOCATION: (8)..(8)
<223> OTHER INFORMATION: Xaa is any amino acid other than Cys, or is
      absent

<400> SEQUENCE: 2

Glu Pro Ala Pro Cys Pro Pro Xaa
1               5

<210> SEQ ID NO 3
<211> LENGTH: 363
<212> TYPE: DNA
<213> ORGANISM: Artificial Sequence
<220> FEATURE:
<223> OTHER INFORMATION: synthetic

<400> SEQUENCE: 3
gctagcacca agggcccatc cgtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacaccaccg tgcccagcac ctgaactcct ggggggaccg     360
tca                                                                   363

<210> SEQ ID NO 4
<211> LENGTH: 375
<212> TYPE: DNA
<213> ORGANISM: Artificial Sequence
<220> FEATURE:
<223> OTHER INFORMATION: synthetic

<400> SEQUENCE: 4
cgaactgtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg tgacaaaact cacacaccac cgtgcccagc acctgaactc     360 ctgggggac cgtca                                                       375

<210> SEQ ID NO 5
<211> LENGTH: 43
<212> TYPE: DNA
<213> ORGANISM: Artificial Sequence
<220> FEATURE:
<223> OTHER INFORMATION: synthetic

<400> SEQUENCE: 5
tgtggctgag aggtgccaga tgtgaagtgc agctggtgga gtc                        43

<210> SEQ ID NO 6
<211> LENGTH: 46
<212> TYPE: DNA
<213> ORGANISM: Artificial Sequence
<220> FEATURE:
<223> OTHER INFORMATION: synthetic
```

<400> SEQUENCE: 6
gacggatggg cccttggtgc tagcactaga cactgtgacc agggta        46

<210> SEQ ID NO 7
<211> LENGTH: 45
<212> TYPE: DNA
<213> ORGANISM: Artificial Sequence
<220> FEATURE:
<223> OTHER INFORMATION: synthetic

<400> SEQUENCE: 7
ctgaactcct gggggaccg tcatgtgaag tgcagctggt ggaat        45

<210> SEQ ID NO 8
<211> LENGTH: 47
<212> TYPE: DNA
<213> ORGANISM: Artificial Sequence
<220> FEATURE:
<223> OTHER INFORMATION: synthetic

<400> SEQUENCE: 8
tgattatgat caatgaattc atcagctaga cactgtcacc agagtgc        47

<210> SEQ ID NO 9
<211> LENGTH: 44
<212> TYPE: DNA
<213> ORGANISM: Artificial Sequence
<220> FEATURE:
<223> OTHER INFORMATION: synthetic

<400> SEQUENCE: 9
taccctggtc acagtgtcta gtgctagcac caagggccca tccg        44

<210> SEQ ID NO 10
<211> LENGTH: 46
<212> TYPE: DNA
<213> ORGANISM: Artificial Sequence
<220> FEATURE:
<223> OTHER INFORMATION: synthetic

<400> SEQUENCE: 10
attccaccag ctgcacttca catgacggtc cccccaggag ttcagg        46

<210> SEQ ID NO 11
<211> LENGTH: 42
<212> TYPE: DNA
<213> ORGANISM: Artificial Sequence
<220> FEATURE:
<223> OTHER INFORMATION: synthetic

<400> SEQUENCE: 11
tgtggctgag aggtgccaga tgtgacattc agatgactca ga        42

<210> SEQ ID NO 12
<211> LENGTH: 47
<212> TYPE: DNA
<213> ORGANISM: Artificial Sequence
<220> FEATURE:
<223> OTHER INFORMATION: synthetic

<400> SEQUENCE: 12
acagatggtg cagccacagt tcgcttgatc tcgactttg tgccctg        47

<210> SEQ ID NO 13
<211> LENGTH: 44

<212> TYPE: DNA
<213> ORGANISM: Artificial Sequence
<220> FEATURE:
<223> OTHER INFORMATION: synthetic

<400> SEQUENCE: 13
ctgaactcct gggggaccg tcagaaatcg tcctcactca gagc            44

<210> SEQ ID NO 14
<211> LENGTH: 44
<212> TYPE: DNA
<213> ORGANISM: Artificial Sequence
<220> FEATURE:
<223> OTHER INFORMATION: synthetic

<400> SEQUENCE: 14
attatgatca atgaattcac tatttgatct caagccgagt gcct            44

<210> SEQ ID NO 15
<211> LENGTH: 44
<212> TYPE: DNA
<213> ORGANISM: Artificial Sequence
<220> FEATURE:
<223> OTHER INFORMATION: synthetic

<400> SEQUENCE: 15
cagggcacaa aagtcgagat caagcgaact gtggctgcac catc            44

<210> SEQ ID NO 16
<211> LENGTH: 47
<212> TYPE: DNA
<213> ORGANISM: Artificial Sequence
<220> FEATURE:
<223> OTHER INFORMATION: synthetic

<400> SEQUENCE: 16
gggctctgag tgaggacgat ttctgacggt ccccccagga gttcagg            47

<210> SEQ ID NO 17
<211> LENGTH: 43
<212> TYPE: DNA
<213> ORGANISM: Artificial Sequence
<220> FEATURE:
<223> OTHER INFORMATION: synthetic

<400> SEQUENCE: 17
ctgaactcct gggggaccg tcaccaggat ggttcttaga ctc            43

<210> SEQ ID NO 18
<211> LENGTH: 48
<212> TYPE: DNA
<213> ORGANISM: Artificial Sequence
<220> FEATURE:
<223> OTHER INFORMATION: synthetic

<400> SEQUENCE: 18
tggctgatta tgatcaatga attctcacac cagggtttgg aactggcc            48

<210> SEQ ID NO 19
<211> LENGTH: 44
<212> TYPE: DNA
<213> ORGANISM: Artificial Sequence
<220> FEATURE:
<223> OTHER INFORMATION: synthetic

<400> SEQUENCE: 19
tgtggctgag aggtgccaga tgtcaggttc agttgcagca gtct            44

<210> SEQ ID NO 20
<211> LENGTH: 45
<212> TYPE: DNA
<213> ORGANISM: Artificial Sequence
<220> FEATURE:
<223> OTHER INFORMATION: synthetic

<400> SEQUENCE: 20
gacggatggg cccttggtgc tagcagaaga gactgtcact gtggt            45

<210> SEQ ID NO 21
<211> LENGTH: 45
<212> TYPE: DNA
<213> ORGANISM: Artificial Sequence
<220> FEATURE:
<223> OTHER INFORMATION: synthetic

<400> SEQUENCE: 21
cctgaactcc tgggggacc gtcagaggtg cagctggttg aatct            45

<210> SEQ ID NO 22
<211> LENGTH: 44
<212> TYPE: DNA
<213> ORGANISM: Artificial Sequence
<220> FEATURE:
<223> OTHER INFORMATION: synthetic

<400> SEQUENCE: 22
gattatgatc aatgaattca tcagctagaa actgtgacca gtgt            44

<210> SEQ ID NO 23
<211> LENGTH: 46
<212> TYPE: DNA
<213> ORGANISM: Artificial Sequence
<220> FEATURE:
<223> OTHER INFORMATION: synthetic

<400> SEQUENCE: 23
ggcaccacag tgacagtctc ttctgctagc accaagggcc catccg            46

<210> SEQ ID NO 24
<211> LENGTH: 45
<212> TYPE: DNA
<213> ORGANISM: Artificial Sequence
<220> FEATURE:
<223> OTHER INFORMATION: synthetic

<400> SEQUENCE: 24
gccagattca accagctgca cctctgacgg tcccccagg agttc            45

<210> SEQ ID NO 25
<211> LENGTH: 44
<212> TYPE: DNA
<213> ORGANISM: Artificial Sequence
<220> FEATURE:
<223> OTHER INFORMATION: synthetic

<400> SEQUENCE: 25
ctgtggctga gaggtgccag atgtgacatc cagctgaccc agtc            44

<210> SEQ ID NO 26

<211> LENGTH: 42
<212> TYPE: DNA
<213> ORGANISM: Artificial Sequence
<220> FEATURE:
<223> OTHER INFORMATION: synthetic

<400> SEQUENCE: 26
gacagatggt gcagccacag ttcgcttgat ttccagcttg gt    42

<210> SEQ ID NO 27
<211> LENGTH: 46
<212> TYPE: DNA
<213> ORGANISM: Artificial Sequence
<220> FEATURE:
<223> OTHER INFORMATION: synthetic

<400> SEQUENCE: 27
cctgaactcc tgggggacc gtcacagaca gtggtcaccc aagagc    46

<210> SEQ ID NO 28
<211> LENGTH: 43
<212> TYPE: DNA
<213> ORGANISM: Artificial Sequence
<220> FEATURE:
<223> OTHER INFORMATION: synthetic

<400> SEQUENCE: 28
tgattatgat caatgaattc actacaaaac tgtcagcttg gtg    43

<210> SEQ ID NO 29
<211> LENGTH: 44
<212> TYPE: DNA
<213> ORGANISM: Artificial Sequence
<220> FEATURE:
<223> OTHER INFORMATION: synthetic

<400> SEQUENCE: 29
ggaggcacca agctggaaat caagcgaact gtggctgcac catc    44

<210> SEQ ID NO 30
<211> LENGTH: 48
<212> TYPE: DNA
<213> ORGANISM: Artificial Sequence
<220> FEATURE:
<223> OTHER INFORMATION: synthetic

<400> SEQUENCE: 30
aggctcttgg gtgaccactg tctgtgacgg tcccccagg agttcagg    48

<210> SEQ ID NO 31
<211> LENGTH: 363
<212> TYPE: DNA
<213> ORGANISM: Artificial Sequence
<220> FEATURE:
<223> OTHER INFORMATION: synthetic

<400> SEQUENCE: 31
gctagcacca agggcccatc cgtcttcccc ctggcaccct cctccaagag cacctctggg    60
ggcacagcgg ccctgggctg cctggtcaag gactacttcc ccgaaccggt gacggtgtcg    120
tggaactcag gcgccctgac cagcggcgtg cacaccttcc cggctgtcct acagtcctca    180
ggactctact ccctcagcag cgtggtgacc gtgccctcca gcagcttggg cacccagacc    240

```
tacatctgca acgtgaatca caagcccagc aacaccaagg tggacaagaa agttgagccc      300
aaatcttgtt caccgggagg gctgctcgaa cctgcaccat gcccgccaac acacactaaa      360
gac                                                                   363
```

<210> SEQ ID NO 32
<211> LENGTH: 375
<212> TYPE: DNA
<213> ORGANISM: Artificial Sequence
<220> FEATURE:
<223> OTHER INFORMATION: synthetic

<400> SEQUENCE: 32

```
cgaactgtgg ctgcaccatc tgtcttcatc ttcccgccat ctgatgagca gttgaaatct       60
ggaactgcct ctgttgtgtg cctgctgaat aacttctatc ccagagaggc caaagtacag      120
tggaaggtgg ataacgccct ccaatcgggt aactcccagg agagtgtcac agagcaggac      180
agcaaggaca gcacctacag cctcagcagc accctgacgc tgagcaaagc agactacgag      240
aaacacaaag tctacgcctg cgaagtcacc catcagggcc tgagctcgcc cgtcacaaag      300
agcttcaaca ggggagagtg ttcaccggga gggctgctcg aacctgcacc atgcccgcca      360
acacacacta aagac                                                      375
```

<210> SEQ ID NO 33
<211> LENGTH: 44
<212> TYPE: DNA
<213> ORGANISM: Artificial Sequence
<220> FEATURE:
<223> OTHER INFORMATION: synthetic

<400> SEQUENCE: 33

```
ctgtggctga gaggtgccag atgtgaggtg cagctggttg aatc                       44
```

<210> SEQ ID NO 34
<211> LENGTH: 60
<212> TYPE: DNA
<213> ORGANISM: Artificial Sequence
<220> FEATURE:
<223> OTHER INFORMATION: synthetic

<400> SEQUENCE: 34

```
tggcgggcat ggtgcaggtt cgagcagccc tcccggtgaa caagatttgg gctcaacttt       60
```

<210> SEQ ID NO 35
<211> LENGTH: 58
<212> TYPE: DNA
<213> ORGANISM: Artificial Sequence
<220> FEATURE:
<223> OTHER INFORMATION: synthetic

<400> SEQUENCE: 35

```
ctcgaacctg caccatgccc gccaacacac actaaagacg aagtgcagct ggttcagt        58
```

<210> SEQ ID NO 36
<211> LENGTH: 47
<212> TYPE: DNA
<213> ORGANISM: Artificial Sequence
<220> FEATURE:
<223> OTHER INFORMATION: synthetic

<400> SEQUENCE: 36

```
ctgattatga tcaatgaatt ctcaagagga cactgtgacc agggtgc                    47
```

<210> SEQ ID NO 37
<211> LENGTH: 43
<212> TYPE: DNA
<213> ORGANISM: Artificial Sequence
<220> FEATURE:
<223> OTHER INFORMATION: synthetic

<400> SEQUENCE: 37
ctgtggctga gaggtgccag atgtgacatc cagatgaccc agt        43

<210> SEQ ID NO 38
<211> LENGTH: 59
<212> TYPE: DNA
<213> ORGANISM: Artificial Sequence
<220> FEATURE:
<223> OTHER INFORMATION: synthetic

<400> SEQUENCE: 38
tggcgggcat ggtgcaggtt cgagcagccc tcccggtgaa cactctcccc tgttgaagc    59

<210> SEQ ID NO 39
<211> LENGTH: 57
<212> TYPE: DNA
<213> ORGANISM: Artificial Sequence
<220> FEATURE:
<223> OTHER INFORMATION: synthetic

<400> SEQUENCE: 39
ctcgaacctg caccatgccc gccaacacac actaaagacg acatcgtgat gacccag      57

<210> SEQ ID NO 40
<211> LENGTH: 49
<212> TYPE: DNA
<213> ORGANISM: Artificial Sequence
<220> FEATURE:
<223> OTHER INFORMATION: synthetic

<400> SEQUENCE: 40
ctgattatga tcaatgaatt ctcacttgat ttccaccttg gtgcctccg             49

<210> SEQ ID NO 41
<211> LENGTH: 48
<212> TYPE: DNA
<213> ORGANISM: Artificial Sequence
<220> FEATURE:
<223> OTHER INFORMATION: synthetic

<400> SEQUENCE: 41
ctgtggctga gaggtgccag atgtgaggtg cagctggttg aatctggc              48

<210> SEQ ID NO 42
<211> LENGTH: 47
<212> TYPE: DNA
<213> ORGANISM: Artificial Sequence
<220> FEATURE:
<223> OTHER INFORMATION: synthetic

<400> SEQUENCE: 42
ggagactggg tcatcacgat gtccaaaact gtcagcttgg tgcctcc              47

<210> SEQ ID NO 43
<211> LENGTH: 47
<212> TYPE: DNA
<213> ORGANISM: Artificial Sequence
<220> FEATURE:
<223> OTHER INFORMATION: synthetic

```
<400> SEQUENCE: 43
aggcaccaag ctgacagttt tggacatcgt gatgacccag tctccag         47

<210> SEQ ID NO 44
<211> LENGTH: 49
<212> TYPE: DNA
<213> ORGANISM: Artificial Sequence
<220> FEATURE:
<223> OTHER INFORMATION: synthetic

<400> SEQUENCE: 44
ctgattatga tcaatgaatt ctcacaccag ggtttggaac tggccggct       49

<210> SEQ ID NO 45
<211> LENGTH: 18
<212> TYPE: PRT
<213> ORGANISM: Artificial Sequence
<220> FEATURE:
<223> OTHER INFORMATION: synthetic

<400> SEQUENCE: 45

Asp Lys Thr His Thr Pro Pro Cys Pro Ala Pro Glu Leu Leu Gly Gly
1               5                   10                  15

Pro Ser

<210> SEQ ID NO 46
<211> LENGTH: 18
<212> TYPE: PRT
<213> ORGANISM: Artificial Sequence
<220> FEATURE:
<223> OTHER INFORMATION: synthetic

<400> SEQUENCE: 46

Ser Pro Gly Gly Leu Leu Glu Pro Ala Pro Cys Pro Pro Thr His Thr
1               5                   10                  15

Lys Asp
```